(12) United States Patent
Wada et al.

(10) Patent No.: US 7,510,988 B2
(45) Date of Patent: Mar. 31, 2009

(54) PARTICULATE WATER-ABSORBING AGENT CONTAINING WATER-ABSORBENT RESIN AS A MAIN COMPONENT

(75) Inventors: Katsuyuki Wada, Himeji (JP); Hiroko Ueda, Himeji (JP); Kazuki Kimura, Toyoka (JP); Kunihiko Ishizaki, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 225 days.

(21) Appl. No.: 11/662,590

(22) PCT Filed: Sep. 22, 2005

(86) PCT No.: PCT/JP2005/018073

§ 371 (c)(1),
(2), (4) Date: Mar. 13, 2007

(87) PCT Pub. No.: WO2006/033477

PCT Pub. Date: Mar. 30, 2006

(65) Prior Publication Data

US 2008/0075937 A1    Mar. 27, 2008

(30) Foreign Application Priority Data

Sep. 24, 2004  (JP) .............................. 2004-276559

(51) Int. Cl.
*B32B 5/18* (2006.01)
*B32B 5/16* (2006.01)

(52) U.S. Cl. ....................... 442/375; 428/206; 525/192; 525/194

(58) Field of Classification Search ................. 442/375; 428/206; 525/192, 194
See application file for complete search history.

(56) References Cited

U.S. PATENT DOCUMENTS

| RE32,649 E | 4/1988 | Brandt et al. |
|---|---|---|
| 5,051,259 A | 9/1991 | Olsen et al. |
| 5,140,076 A | 8/1992 | Hatsuda et al. |
| 5,147,343 A | 9/1992 | Kellenberger |
| 5,149,335 A | 9/1992 | Kellenberger et al. |
| 5,409,771 A | 4/1995 | Dahmen et al. |
| 5,419,956 A | 5/1995 | Roe |
| 5,453,323 A | 9/1995 | Chambers et al. |
| 5,462,972 A | 10/1995 | Smith et al. |
| 5,562,646 A | 10/1996 | Goldman et al. |
| 5,601,452 A | 2/1997 | Ruffa |
| 5,669,894 A | 9/1997 | Goldman et al. |
| 5,712,316 A | 1/1998 | Dahmen et al. |
| 5,797,893 A | 8/1998 | Wada et al. |
| 5,994,440 A | 11/1999 | Staples et al. |
| 6,087,002 A | 7/2000 | Kimura et al. |
| 6,127,454 A | 10/2000 | Wada et al. |
| 6,150,582 A | 11/2000 | Wada et al. |
| RE37,021 E | 1/2001 | Aida |
| 6,184,433 B1 | 2/2001 | Harada et al. |
| 6,194,531 B1 | 2/2001 | Hatsuda et al. |
| 6,297,335 B1 | 10/2001 | Funk et al. |
| 6,388,000 B1 | 5/2002 | Irie et al. |
| 6,414,214 B1 | 7/2002 | Engelhardt et al. |
| 6,444,744 B1 | 9/2002 | Fujimaru et al. |
| 2002/0128618 A1 | 9/2002 | Frenz et al. |
| 2002/0165288 A1 | 11/2002 | Frenz et al. |
| 2004/0181031 A1 | 9/2004 | Nogi et al. |
| 2005/0209411 A1 | 9/2005 | Nestler et al. |

FOREIGN PATENT DOCUMENTS

| DE | 10221202 | 7/2003 |
|---|---|---|
| EP | 0532002 | 3/1993 |
| EP | 0605215 | 7/1994 |
| EP | 0629441 | 12/1994 |
| EP | 0707603 | 4/1996 |
| EP | 0712659 | 5/1996 |
| EP | 0937739 | 8/1999 |
| EP | 0940148 | 9/1999 |
| EP | 1029886 | 8/2000 |
| EP | 1153656 | 11/2001 |
| GB | 235307 | 3/1924 |
| GB | 2267094 | 11/1996 |
| JP | 60-158861 | 8/1985 |
| JP | 11-241030 | 9/1999 |
| WO | WO 02/053198 | 7/2002 |
| WO | WO 03/095510 | 11/2003 |
| WO | WO 2004/006915 | 8/2004 |

OTHER PUBLICATIONS

International Search Report (PCT/ISA/210).

*Primary Examiner*—Lynda Salvatore
(74) *Attorney, Agent, or Firm*—Harness, Dickey & Pierce, P.L.C.

(57) ABSTRACT

In at least one embodiment, a particulate water-absorbing agent is provided which not only ensures the many conventional physical properties (absorption rate, centrifuge retention capacity, absorbency against pressure, particle size distribution etc.) but also prevents odor which is generated after the resin is swollen by absorption. The water absorbent agent of an embodiment of the present invention therefore does not cause odor in actual use. As a result of intensive study of the foregoing problem, an embodiment of the present invention offers a way of controlling a specific odor component, which is generated from impurities and/or by-product derived from the raw material, after the high temperature process. In this way, an embodiment of the present invention successfully provides a water absorbent agent not causing odor after the resin is swollen by absorption.

13 Claims, No Drawings

PARTICULATE WATER-ABSORBING AGENT CONTAINING WATER-ABSORBENT RESIN AS A MAIN COMPONENT

TECHNICAL FIELD

The present invention relates to a particulate water-absorbing agent containing a water-absorbent resin as a main component. More specifically, the present invention relates to a particulate water-absorbing agent used for an absorbent structure of an absorbent article, such as disposal diaper. The particulate water-absorbing agent of the present invention is superior in absorptive ability, and causes no odor or ethylene glycol. The combination of these three benefits has never attained by the conventional agent.

BACKGROUND ART

Recently, a water-absorbent resin (or a particulate water-absorbing agent containing an absorbing resin) and a hydrophilic fiber such as pulp are widely used as a main construction raw material of sanitary raw materials, such as disposal diapers, sanitary napkins, incontinence pads, in order to absorb body fluids. The water-absorbent resin is mainly made of (i) cross-linked partially neutralized polyacrylic acid; (ii) a hydrolyzed starch-acrylic acid graft polymer; (iii) a saponified vinyl acetate-acrylic acid ester copolymer; (iv) hydrolyzed acrylonitrile copolymer or cross-linked acrylonitrile copolymer; (v) hydrolyzed acrylamide copolymer or cross-linked acrylamide copolymer; (vi) a cross-linked cationic monomer and the like.

There have conventionally been needs for a water-absorbent resin having the following absorption properties: (i) a high absorption capacity for a aqueous liquid such as a body fluid, (ii) an excellent absorption rate, (iii) excellent liquid-permeability, and (iv) excellent gel strength of a swollen gel, and (v) an excellent suction amount from a wet substrate containing aqueous liquid, (vi) and the like. To meet these demands, a recent particulate water-absorbing agent has a particular physical property.

In view of the indispensable demands for high water absorption capacity and high liquid permeability under pressure, and needs for water-absorbent resin particles significantly narrow particle size distribution, or a water-absorbent resin particles having a high absorption capacity and low water-soluble component, many parameter patents and measurement methods have been applied so as to regulate the various physicalities of water-absorbent resin. The following documents 1 through 39 are example of the patents.

Document 1 discloses a water-absorbent resin superior in gel strength, water-soluble component, and water absorption capacity. Document 2 discloses a water-absorbent resin superior in liquid-permeability without load, absorption rate, and absorption capacity. Documents 3 through 6 disclose techniques of making specific particle size distribution. Further, many other documents suggest a water-absorbent resin superior in absorbency against pressure under different pressures, as well as measurements methods for checking the absorbency against pressure. The following Documents 7 through 16, 38 and 39 suggests water-absorbent resins, some of which are superior solely in absorbency against pressure, and others are superior both in absorbency against pressure and in other physical properties.

Further, Documents 17 and 18 suggest a water-absorbent resin which has excellent damage-resistance of its properties, Document 19 suggests a water-absorbing agent whose dust-size particle amount is specified, and Document 20 suggests a water-absorbent resin causing less coloring. Further, Documents 21 and 22 suggest a water-absorbent resin superior in water absorption amount and gel-stability against an L-ascorbic acid aqueous solution or the like for regulating urine-resistance, and Document 23 suggests a water-absorbent resin superior in air permeability. Furthermore, Document 24 suggests a water-absorbent resin having less residual monomer.

Further, Documents 25 through 32 and some other documents suggest that a water-absorbent resin with a specific physical property is useful for an absorbent article (disposal diaper) with a specific physical property, structure and polymer content. Document 33 etc. suggest a method for surface-cross-linking which is performed by pulverizing at least a part of resin particles.

Further, in recent years, the thickness of a sanitary raw material, such as a disposal diaper, tends to be reduced, making water-absorbent resin content higher, which increases a demand for relieving odor from the water-absorbent resin. To relieve the odor, there has been suggested use of various deodorant agents and/or antibacterial agent together with a water-absorbent resin, so as to give a deodorant property to the water-absorbent resin. Examples of this product includes a water-absorbent resin composition made of a water-absorbent resin and an extract from leaves of a theaceous plant (for example, Document 34), or a water-absorbent resin composition made of a water-absorbent resin having a specific property and an extract from an aiculilignosa (for example, Document 35). Further, some recent technologies (e.g. Document 36) focus on acetic acid or propionic acid, which are impurities in the acrylic acid, as a cause of odor of water-absorbent resin. Further, other technology relating to a residual monomer (e.g. Document 37) focuses on β-hydroxypropionic acid, which is an impurity in the acrylate.

As described, there have been many technologies for meeting various demands regarding property of water-absorbent resin. However, those conventional water-absorbent resins can no longer ensure their effects in the recent absorbent structure (such as disposal diaper) which uses a greater amount of water-absorbent resin, that is, has a higher content (higher weight ratio) of water-absorbent resin. Moreover, as the usage amount (content) of water-absorbent resin for an absorbent structure, such as disposal diaper, is increasing, the deodorant property has become an important factor, but trials of various deodorant agents, which are used to give the deodorant property direct onto the absorbing agent, have not made satisfactory results of obtaining sufficient deodorant property.

Further, an absorbent article, such as disposal diaper, has been having defects of coarse feeling of absorbent particles, and particle segregation which makes particle size uneven. In view of these problems, there is another demand for water-absorbent resin particles having narrower particle size distribution.

However, any of conventional water-absorbent resins have not satisfied all of these demands in actual use: reduced odor, excellent absorption capacity, narrower particle size distribution and less particle segregation.

In view of this, the present invention provides a water-absorbent resin satisfying all of the demands in actual use: reduced odor, excellent absorption capacity, narrower particle size distribution and less particle segregation. With this water-absorbent resin, the present invention also provides an absorbing agent which can be used as a comfortable absorbent article ensuring high physical property and safety and has a composition not causing odor after swelling.

[Document 1] U.S. re-issued Pat. No. Re32649 Specification

[Document 2] UK Patent No. 2267094 B Specification

[Document 3] U.S. Pat. No. 5,051,259 Specification

[Document 4] U.S. Pat. No. 5,419,956 Specification

[Document 5] U.S. Pat. No. 6,087,002 Specification

[Document 6] EP Patent No. 0629441 Specification

[Document 7] EP Patent No. 0707603 Specification
[Document 8] EP Patent No. 0712659 Specification
[Document 9] EP Patent No. 1029886 Specification
[Document 10] U.S. Pat. No. 5,462,972 Specification
[Document 11] U.S. Pat. No. 5,453,323 Specification
[Document 12] U.S. Pat. No. 5,797,893 Specification
[Document 13] U.S. Pat. No. 6,127,454 Specification
[Document 14] U.S. Pat. No. 6,184,433 Specification
[Document 15] U.S. Pat. No. 6,297,335 Specification
[Document 16] U.S. re-issued Pat. No. Re37021 Specification
[Document 17] U.S. Pat. No. 5,140,076 Specification
[Document 18] U.S. Pat. No. 6,414,214B1 Specification
[Document 19] U.S. Pat. No. 5,994,440 Specification
[Document 20] U.S. Pat. No. 6,444,744 Specification
[Document 21] U.S. Pat. No. 6,194,531 Specification
[Document 22] EP Patent No. 0940148 Specification
[Document 23] EP Patent No. 1153656 Specification
[Document 24] EP Patent No. 0605215 Specification
[Document 25] U.S. Pat. No. 5,147,343 Specification
[Document 26] U.S. Pat. No. 5,149,335 Specification
[Document 27] EP Patent No. 0532002 Specification
[Document 28] U.S. Pat. No. 5,601,452 Specification
[Document 29] U.S. Pat. No. 5,562,646 Specification
[Document 30] U.S. Pat. No. 5,669,894 Specification
[Document 31] U.S. Pat. No. 6,150,582 Specification
[Document 32] International Publication No. 02/053198 Pamphlet
[Document 33] EP Patent No. 0937739 Specification
[Document 34] Japanese unexamined patent publication Tokukaisho 60-158861
[Document 35] Japanese unexamined patent publication Tokukaihei 11-241030
[Document 36] International Publication No. 03/095510 Pamphlet
[Document 37] U.S. Pat. No. 6,388,000 Specification
[Document 38] U.S. Pat. No. 5,409,771 Specification
[Document 39] UK Patent No. 235307 Specification

DISCLOSURE OF INVENTION

In order to solve the foregoing problems, the inventors of the present invention have studied the deodorant property (for example, by the use of deodorant agent) of the water-absorbent resin (water-absorbing agent) as its additional function, and found an unexpected fact that a water-absorbent resin itself generates a characteristic odor after swelling, which has been actually decreasing the deodorant property of the absorbing agent when used as a product such as disposal diaper.

Then, the inventors have further studied the cause of the characteristic odor of the water-absorbent resin, and found the following fact. What they found was a fact that a product made of water-absorbent resin obtained with use of a particular surface-cross-linking agent (surface-cross-linking agent which forms ester bond with a carboxyl group) and having high absorbency against pressure or without pressure generates the characteristic odor, thereby decreasing the performance as a water-absorbing agent of disposal diaper or the like in actual use even though the raw material of water-absorbent resin has no odor itself. The inventors further found that, by eliminating such an odor of water-absorbent resin, the physical property of resin increases and the resin becomes applicable for an absorbent article, such as disposal diaper. This high-performance absorbent article, such as disposal diaper, is made of the foregoing water absorbing agent, which uses a surface-cross-linking agent forming ester bond with a carboxyl group, and ensures high absorption capacity as a result of high-temperature processing, and reduced odor. These two characteristics have been incompatible in the conventional products.

In the process of studying a specific surface-cross-linking agent not causing much of odor, the inventors further found that, depending on the type of cross-linking agent, some water-absorbent resins contain residual ethylene glycol, which is generated as a by-product, even though they are produced using no ethylene glycol as a monomer or a crosslinking agent. If the water-absorbent resin contains such residual ethylene glycol, the safety of the resin is not fully ensured. Then, after further study of the origin of residual ethylene glycol, they found that it derives from impurities or decomposition products of the surface-cross-linking agent used for the raw material (particularly, ethylene glycol derivative, such as ethylene carbonate, polyethylene glycol, etc.). Further, if alkylene carbonate (particularly, ethylene carbonate) is used as a surface-cross-linking agent so as to increase the physical property (particularly, liquid-permeability under pressure or absorbency against pressure), it is necessary to use a large amount of cross-linking agent and to carry out a reaction process at high temperature. Thus, even when no ethylene glycol is used for the raw material, or even when alkylene carbonate such as ethylene carbonate does not contain ethylene glycol, the absorbent article completed as a commodity contains ethylene glycol as a by-product. The inventors finally solved the problem of safety caused by ethylene glycol, and found a way of obtaining an absorbent structure (such as disposal diaper) with superior physical property (particularly, liquid-permeability under pressure or absorbency against pressure) with the use of alkylene carbonate in a surface-cross-linking agent, as well as sufficient safety, which have been incompatible in the conventional products.

Further, the inventors also worked on the problem of a large amount of dust-size particle and particle segregation, which are produced when the water-absorbent resin is pulverized to reduce particle size. As a result, they found that the average particle diameter, the amount of dust-size particle, and the particle size distribution are important factors for particulate water-absorbent resin to ensure its physical property as an absorbent structure (such as disposal diaper). Accordingly, the inventors found a way of restricting these factors: the average particle diameter, the amount of dust-size particle, and the particle size distribution, of water-absorbent resin particle, which are incompatible physical properties, thereby obtaining particulate water-absorbent resin with narrow particle size distribution and small particle segregation.

With such new findings (1)a desired surface-cross-linking agent, desires physical property, and allowable level of odor are incompatible, 2) the high physical property given by surface-cross-linking agent such as alkylene carbonate results in by-product of ethylene glycol which has safety issue, 3) a desired average particle diameter and allowable amount of dust-size particle are incompatible, 4) the five physical properties: centrifuge retention capacity (CRC), absorbency against pressure (AAP), mass average particle diameter, the amount of particles less than 150 μm in the particulate water-absorbing agent, logarithmic standard deviation of particle size distribution, are important factors for the use of absorbent structure such as disposal diaper), the inventors have made the present invention, which provides a practically ideal particulate water-absorbing agent, which meets at least the five specific physical properties.

More specifically, the particulate water-absorbing agent (first water-absorbing agent) according to the present invention contains, as a main component, a particulate polycarboxylic acid water-absorbent resin surface-cross-linked by a surface-cross-linking agent which forms ester bond with a carboxyl group, the particulate water-absorbing agent satisfying following conditions:

(a) a centrifuge retention capacity (CRC) for a physiological saline solution being not less than 27 g/g;

(b) an absorbency against pressure (AAP) of 4.8 kPa for the physiological saline solution being not less than 20 g/g;

(c) a mass average particle diameter (D50) being 200-450 μm;

(d) an amount of particles smaller than 150 μm in the particulate water-absorbing agent being 0-5% by mass;

(e) a logarithmic standard deviation (σζ) of particle size distribution being 0.20-0.40; and (f) a content of an alcohol volatile substance evaporated from the particulate water-absorbing agent being 0-10 ppm, the content being measured by a gas detecting tube as an atmosphere concentration.

The particulate water-absorbing agent (second water-absorbing agent) according to the present invention contains, as a main component, a particulate polycarboxylic acid water-absorbent resin surface-cross-linked by a surface-cross-linking agent which contains alkylene carbonate and forms ester bond with a carboxyl group, the particulate water-absorbing agent satisfying following conditions:

(a) a centrifuge retention capacity (CRC) for a physiological saline solution being not less than 27 g/g;

(b) an absorbency against pressure (AAP) of 4.8 kPa for the physiological saline solution being not less than 20 g/g;

(c) a mass average particle diameter (D50) being 200-450 μm;

(d) an amount of particles smaller than 150 μm in the particulate water-absorbing agent being 0-5% by mass;

(e) a logarithmic standard deviation (σζ) of particle size distribution being 0.20-0.40; and (g) a content (determined by HPLC) of residual ethylene glycol in the particulate water-absorbing agent being 0-40 ppm.

The particulate water-absorbing agent and the manufacturing method thereof meet all of the requirements of particulate water-absorbing agent in actual use: reduced odor, safety, excellent absorption capacity, narrow particle size distribution and less particle segregation. Accordingly, the water-absorbing agent can be used for a comfortable absorbent article ensuring high physical property, safety, superior absorption ability and causes less odor in actual use, especially when used as high-content disposal diaper (a single diaper sheet contain a large amount of water-absorbent resin), which has conventionally been having the odor problem.

BEST MODE FOR CARRYING OUT THE INVENTION

The following explanation deals with the particulate water-absorbing agent of the present invention, the water-absorbent resin used for the particulate water-absorbing agent, and the raw materials, reaction condition etc. Further, in the present invention, specific measurement methods, which are described later in "Examples", are used for measurements of (a) centrifuge retention capacity for physiological saline solution without load (CRC), (b) absorbency against pressure of 4.8 kPa for physiological saline solution (AAP), (c) mass average particle diameter (D50), (d) amount of particles smaller than 150 μm in the particulate water-absorbing agent, (e) logarithmic standard deviation (σζ) of particle size distribution, (f) content of an alcohol volatile substance evaporated from the particulate water-absorbing agent, (g) content of residual ethylene glycol in the particulate water-absorbing agent, (h) amount of volatile sulfuric substance evaporated from the particulate water-absorbing agent (amount of volatile sulfur containing component), (i) total content (amount) of acrylic acid, acetic acid, or propionic acid in the particulate water-absorbing agent, and (j) white index.

Note that, in the present specification, "% by mass" and "% by weight" are identical in sense and thus replaceable.

(1) Water-absorbent Resin

A water-absorbent resin in the present invention designates a cross-linked polymer forming hydro-gel, which is swollen by water and insoluble in water. Here, the swelling property by water denotes an ability of absorbing a large amount of water, for example, 5 times, preferably 50 times to 1000 times ion exchange water of tare mass. The water insolubility denotes the property in which water-soluble component is 50% by weight or less of the substance. To check these conditions, the measurement method used in "Examples" of the present invention, ERT (EDENA Recommended Test Method) 441.1-99 or 470.1-99 of EDANA (European Disposables and Nonwovens Association) may be used.

To meet the foregoing condition, the water-absorbent resin of the present invention is a water-absorbent resin obtained by drying a cross-linked polymer, which is produced by cross-link-polymerizing of an unsaturated monomer containing an acid and/or the salt thereof. One preferable example of such a resin may be a polycarboxylic acid water-absorbent resin, particularly a partially neutralized polyacrylic acid polymer obtained by polymerization/cross-linking of an unsaturated monomer, which contains an acrylic acid and/or the salt thereof (neutralized) as main components.

Further, the water-absorbent resin used in the present invention is not limited to the one manufactured by the manufacturing method disclosed in this application, and may be any resin obtained by drying a cross-linked polymer containing a structure unit derived from an unsaturated monomer, which is described later. The structure unit derived from an unsaturated monomer corresponds to a structure in which polymerizable double bond of each monomer is opened, for example, by polymerization reaction (that is, a double bond (—C=C—) became a single bond (—C—C—)).

(2) Particulate Water-absorbing Agent and Manufacturing Method Thereof

The particulate water-absorbing agent of the present invention means an absorption/solidification agent for an aqueous liquid. The agent contains a water-absorbent resin as a main component and may contain a small amount of additives and/or water as required. The content of water-absorbent resin in particulate water-absorbing agent of 100% by mass is 70-100%, preferably 80-100%, more preferably 90-100% by mass. Apart from the water-absorbent resin, the particulate water-absorbing agent mainly contains water and the various additives described later. Further, apart from water, the aqueous liquid may be any liquid containing water, such as urine, blood, feces, waste fluid, moisture/steam, ice, mixture of water and organic and/or inorganic solvent, rainwater, or groundwater. However, urine, particularly human urine, is most typical.

The particulate water-absorbing agent of the present invention can be manufactured through any methods ensuring the foregoing physical properties. For example, the surface-cross-linking may be performed after the particles are into a certain particle size. The following "Manufacturing method 1" describes a further preferable example. Similarly, "Manufacturing method 2", "Manufacturing method 3", and "Manufacturing method 4" are also available.

[Manufacturing Method 1]

A water-absorbent resin with a specific particle size distribution and a specific absorption capacity is produced first, and then the vicinity of the surface of this water-absorbent resin is heated after mixed with a surface-cross-linking agent which causes an ester bond. During or after the heat treatment, the water-absorbent resin is exposed to airflow at 60° C. or more. In this method, the purity of the raw material, that is an acrylic acid, is preferably specified to the range described later.

[Manufacturing Method 2]

An unsaturated monomer aqueous solution, which contains a non-neutralized acrylic acid and/or the salt thereof as a main component of the monomer, is subjected to cross-link-polymerizing in the presence of an internal-cross-linking agent and, if required, also a chain transfer agent, so as to obtain a water-absorbent resin having a specific absorption capacity. The particle size distribution of the water-absorbent resin is then adjusted. The resulting cross-linked polymer having a specific absorption capacity and a specific particle size distribution is subjected to surface-cross-linking.

[Manufacturing Method 3]

An unsaturated monomer aqueous solution, which contains a non-neutralized acrylic acid as a main component, is subjected to cross-link-polymerizing in the presence of an internal-cross-linking agent, so as to obtain a water-absorbent resin having a specific absorption capacity. The water-absorbent resin is further neutralized and the particle size distribution is adjusted. The resulting cross-linked polymer having a specific absorption capacity and a specific particle size distribution is subjected to surface-cross-linking.

[Manufacturing Method 4]

An unsaturated monomer aqueous solution, which contains a non-neutralized acrylic acid and/or the salt thereof as a main component of the monomer, is subjected to cross-link-polymerizing in the presence of an internal-cross-linking agent, so as to obtain a water-absorbent resin having a specific absorption capacity. The particle size distribution of the water-absorbent resin is then adjusted. The resulting cross-linked polymer having a specific absorption capacity and a specific particle size distribution is subjected to surface-cross-linking. If required, a chelator is added during the polymerization, or before, after or during the surface-cross-linking.

The following explains a particulate water-absorbing agent of the present invention and a manufacturing method thereof.

(3) Unsaturated Monomer

[Acrylic Acid]

For the unsaturated monomer (hereinafter refereed to as monomer according to the context), an acrylic acid and/or the salt thereof is preferably used. Further, an acrylic acid having a specific purity, that is, an acrylic acid having a specific amount of a specific compound is particularly suitable for the particulate water-absorbing agent of the present invention. An example of the acrylic acid may be one containing one or plural of the compounds selected from: 10-200 ppm of methoxyphenol, 0-10000 ppm of acetic acid and propionic acid combined together, 0-1000 ppm of acrylic acid dimer, 0-10 ppm of furfural, and 0-10 ppm of protoanemonin.

More preferably, the acrylic acid contains acetic acid and propionic acid in a range of 1000-0 ppm in total, and acrylic acid dimer in a range of 1000-0 ppm. Further, each content of the acetic acid and propionic acid in total, and the acrylic acid dimer are preferably not more than 500 ppm, further preferably not more than 300 ppm and still further preferably not more than 100 ppm. Each content of furfural and protoanemonin is preferably not more than 5 ppm and more preferably not more than 1 ppm. When the amount of acetic acid and propionic acid in total, and the amount of acrylic acid dimmer fall out of a certain range, these compounds may cause odor or residual monomer, and therefore it is not a suitable raw material of the particulate water-absorbing agent of the present invention which contains only a small amount of volatile organic matter, such as alcohol volatile substance (alcohol-basis conversion). Further, when the acrylic acid contains an excessive amount of furfural or protoanemonin, it is not suitable to make a water-absorbing agent ensuring high absorption capacity. P-methoxyphenol is useful for controlling/prompting the polymerization. The amount of p-methoxyphenol is generally not more than 200 ppm, preferably in a range of 20-160 ppm, more preferably in a range of 30-100 ppm.

Such an acrylic acid can be obtained by controlling the condition in oxidizing the acrylic acid, or by restricting condition for distillation or crystallization. When the acrylic acid is purified by distillation, the rectification degree can be increased, for example by increasing number of theoretical plates (e.g. use 6-20 more plates) or by increasing the reflux ratio. Further, when the acrylic acid is purified by crystallization, the rectification degree can be increased, for example, by increasing number of crystallization processes (e.g. carry out 3-10 more crystallization processes). Note that, the acrylic acid may be purified by a method using both distillation and crystallization. Further, after the acrylic acid is produced, the temperature is decreased (10-25° C.) to make a good conservation condition.

[Other Monomers]

Other monomer than the acrylic acid may be used as the monomer for constituting the water-absorbent resin of the present invention, either as a co-polymerization component, or as an only monomer for constituting the water-absorbent resin. Examples of the other monomer include water soluble or hydrophobic unsaturated monomer, such as methacrylic acid, maleic acid (or maleic anhydride), fumaric acid, crotonic acid, itaconic acid, vinyl sulfonic acid, 2-(meth)acrylamide-2-methylpropanesulfonic acids, (meth)acryloxyalkane sulfonic acids and their alkali metal salts, their ammonium salts, N-vinyl-2-pyridone, N-vinyl acetamide, (meth)acrylamide, N-isopropyl (meth)acrylamide, N,N-dimethyl (meth)acrylamide, 2-hydroxyethyl(meth)acrylate, methoxypolyethylene glycol(meth)acrylate, polyethylene glycol (meth)acrylate, isobutylene, lauryl(meth)acrylate. Note that, the "water soluble" in the present invention means a property at least 1 g of which is dissolved in 100 g of water at room temperature.

Further, aside from the foregoing cross-linked polymer made from an unsaturated monomer, a polycarboxylic acid water-absorbent resin may be used. Examples of this type of resin include cross-linked polyamino acid (e.g. polyaspartic acid) or a cross-linked carboxylic polymer (e.g. carboxymethylcellulose, carboxymethyl starch).

In case of using an unsaturated monomer other than an acrylic acid (salt), it is preferable in view of the object of the present invention that the content of the monomer other than the acrylic acid (salt) is 0-30 mol %, more preferably 0-10 mol %, further preferably 0-5 mol % with respect to the total amount of the acrylic acid and its salt that are used as main components.

Note that, in case where the monomer is an unsaturated monomer having an acid group, its salt may be an alkali metal salt, an alkaline earth metal salt, or an ammonium salt. Meanwhile a sodium salt or a potassium salt is particularly preferable because (i) the sodium salt and potassium salt are easily obtained in dust-size particle, (ii) the sodium salt and potassium salt are harmless, and (iii) use of the sodium salt and/or potassium salt gives better property to the water-absorbent resin obtained and affects the other advantages.

Further, the unsaturated monomer containing an acid group (such as an acrylic acid) is preferably neutralized in terms of both physical property and pH ratio: the neutralization ratio of the acid group is generally in a range of 20 to 100 mol %, more preferably in a range of 30 to 95 mol %, further preferably in a range of 40 to 80 mol %. The neutralization may be carried out in a stage of a monomer, or in a stage of polymer as with [manufacturing method 3], or both.

(4) Cross-Linking Monomer (Internal-Cross-Linking Agent

The water-absorbent resin of the present invention is a cross-linked polymer obtained by drying a cross-linked polymer, which is made by polymerizing the unsaturated monomer. Thus, the internally cross-linking structure of the water-absorbent resin may be obtained by causing an unsaturated monomer to be self-cross-linked without using a cross-linking monomer. However, it is more preferable that the water-absorbent resin is obtained by copolymerizing or reacting the unsaturated monomer with the cross-linking monomer (also referred to as an internal-cross-linking agent of water-absorbent resin). Here, the cross-linking monomer which functions as an internal-cross-linking agent has two or more polymerizable unsaturated groups contained in one molecule thereof or has two or more reactive groups. When the water-absorbent resin has water-insolubility and a water-swelling property, it is regarded as having an internally cross-linking structure.

Examples of such an internal-cross-linking agent includes N,N'-methylenebis(meth)acrylamide, (poly)ethyleneglycol di(meth)acrylate, (poly)propyleneglycol di(meth)acrylate, trimethylolpropanetri(meth)acrylate, glyceroltri(meth)acrylate, glycerolacrylatemethacrylate, ethyleneoxide modified trimethylolpropanetri(meth)acrylate, pentaerythritolhexa(meth)acrylate, triallyl cyanurate, triallyl isocyanurate, triallyl phosphate, triallyl amine, poly(meth)allyloxyalkane, (poly)ethyleneglycoldiglycidylether, glyceroldiglycidylether, ethylene glycol, polyethylene glycol, propylene glycol, glycerine, pentaerythritol, ethylenediamine, ethylene carbonate, propylene carbonate, polyethyleneimine, and glycidyl(meth)acrylate, and the like.

These internal-cross-linking agents may be used either individually or in a suitable combination of two or more kinds. The internal-cross-linking agent may be added to the reaction system either at once or in separate doses. When using one or more internal-cross-linking agents, it is preferable that a cross-linking monomer including not less than two polymerizable unsaturated groups is always used for the polymerization, taking into account the absorption properties or other properties of the product water-absorbing agent.

For desirable properties of the water-absorbent resin, the amount of internal-cross-linking agent used is preferably 0.001 to 2 mol %, more preferably 0.005 to 0.5 mol %, further preferably 0.01 to 0.2 mol %, and particularly preferably 0.03 to 0.15 mol %, all with respect to the unsaturated monomer (except for the internal-cross-linking agent). In case the amount of the internal-cross-linking agent to be added is less than 0.001 mol %, or in case the amount is more than 2 mol %, there is a possibility that a sufficient absorption properties cannot be attained, so that this is not preferable. More Specifically, in case the amount of the internal-cross-linking agent to be added is less than the foregoing value, the cross-linking structure is not fully formed, resulting in failure of production of the cross-linked polymer described in (1), which is swollen by water and insoluble in water. On the other hand, in case the amount is more than the foregoing value, the water-soluble component is reduced, but also absorption capacity of the water-absorbent resin or absorbing agent is reduced, thereby decreasing absorption capacity of the absorbent article when realized as disposal diaper or the like.

When the internal-cross-linking agent is used to form a cross-linked structure inside the water-absorbent resin, the internal-cross-linking agent is added to the reaction system before, during, or after the polymerization of the unsaturated monomer, or after the neutralization of the unsaturated monomer or the polymer.

(5) Polymerization Initiator

The water-absorbent resin of the present invention is obtained by using a polymerization initiator in polymerizing the unsaturated monomer. As the polymerization initiator, for example, a radical polymerization initiator such as potassium persulfate, ammonium persulfate, sodium persulfate, potassium peracetate, sodium peracetate, potassium percarbonate, sodium percarbonate, t-butylhydroperoxide, hydrogen peroxide, and 2,2'-azobis (2-amidino-propane) dihydrochloride, or a photopolymerization initiator such as 2-hydroxy-2-methyl-1-phenyl-propane-1-one may be used. It is preferable that an amount of the polymerization initiator is usually in a range of 0.001 mol % to 2 mol %, and preferably in a range of 0.01 mol % to 0.1 mol % in terms of physical property with respect to the total number of moles of all the unsaturated monomers used to obtain the water-absorbent resin. If the polymerization initiator is less than 0.001 mol %, an amount of monomer not reacted and left over (residual monomer amount) is increased. On the other hand, if the amount of the polymerization initiator is more than 2 mol %, it becomes difficult to control the polymerization. Thus, neither of the amount of the polymerization initiator less than 0.001 mol % nor the amount more than 2 mol % is preferable.

(6) Polymerization Method and Polymerization Solution

For the polymerization of the unsaturated monomer to obtain the water-absorbent resin of the present invention, bulk polymerization or precipitation polymerization may be performed. However, in consideration of the desired physical properties of the water-absorbent resin, more preferable methods of polymerization are aqueous polymerization and reversed suspension polymerization, using an aqueous solution of the monomer. When an aqueous solution of the monomer is used, the concentration of the monomer in the aqueous solution (hereinafter, "monomer aqueous solution") is determined in accordance with a temperature of the solution and a type of the monomer and hence is not limited to any particular value. However, the concentration is preferably within 10 to 70% by mass, and more preferably 20 to 60% by mass, when the polymerization is carried out with a previously-neutralized unsaturated monomer containing an acid group by combining "Manufacturing methods 1 and 2", or "Manufacturing methods 1 and 4" (neutralization polymerization). Further, the aqueous polymerization may be carried out not only with water but also with any other additional solvents.

The polymerization of the monomer is initiated by using the aforementioned polymerization initiator. Besides the polymerization initiator, an activating energy ray, such as ultraviolet light, an electron ray, and a γ ray, may be used solely or in combination with the polymerization initiator. Note that, which temperature the polymerization is initiated is selected as required depending on which kind of polymerization initiator is used. However, it is preferable that the polymerization is initiated at a temperature in a range of 15° C. to 130° C., and it is more preferable that the polymerization is initiated at a temperature in a range of 20° C. to 120° C.

The reverse phase suspension polymerization is a polymerization method that is carried out by suspending the monomer aqueous solution in a hydrophobic organic solvent. For example, the reverse phase suspension polymerization is described in documents such as U.S. Pat. Nos. 4,093,776, 4,367,323, 4,446,261, 4,683,274, and 5,244,735, for example. Further, the aqueous solution polymerization is a polymerization method in which the polymerization is carried out by using the monomer aqueous solution without using a dispersion solvent. For example, the aqueous solution polymerization is described in documents such as U.S. Pat. Nos. 4,625,001, 4,873,299, 4,286,082, 4,973,632, 4,985,518, 5,124,416, 5,250,640, 5,264,495, 5,145,906, and 5,380,808, and documents such as European Patent Nos. 0,811,636, 0,955,086, and 0,922,717. Note that, when performing aqueous polymerization, a solvent other than water may be used as required. The type of solvent used together is not particularly limited. The monomer and/or the initiator disclosed in those documents are also applicable in the present invention.

(7) Other Polymerization Methods (a) Polymerization of an unsaturated monomer containing a non-neutralized carboxylic acid (acrylic acid) group as a main component The polymerization method described in (6) is generally performed with an unsaturated monomer containing a previously-neutralized acid group (neutralization polymerization). However, as with the Manufacturing method 3, it is also allowable that the polymerization is performed with an unsaturated monomer containing a non-neutralized acid group, in particular, a non-neutralized acrylic acid, as a main component. In this case, the acid group is neutralized after the polymerization. This method is known as "acid polymerization and post-neutralization".

For example, in the "Manufacturing method 3", a specifically-concentrated unsaturated monomer aqueous solution, which contains a non-neutralized acrylic acid as a main component, is subjected to cross-link-polymerization in the presence of an internal-cross-linking agent, so as to obtain a water-absorbent resin having a specific absorption capacity. The water-absorbent resin is further neutralized and the particle size distribution is adjusted. The resulting cross-linked polymer having a specific absorption capacity and a specific particle size distribution is subjected to surface-cross-linking.

In this "acid polymerization and post-neutralization", the water-absorbent resin used in the present invention is obtained by adding an univalent salt, in particular, alkali metallic salt, to a cross-linked polymer so that a part of acid groups of the polymer is neutralized to alkali metallic salt. The cross-linked polymer was prepared by polymerization of an unsaturated monomer containing a non-neutralized acrylic acid as a main component. The content of the non-neutralized acrylic acid is preferably 30-100 mol %, more preferably 90-100 mol %, further preferably 100 mol %. With this water-absorbent resin thus obtained by the "acid polymerization and post-neutralization", the property as an absorbing agent and stability to urine are ensured for the particulate water-absorbing agent of the present invention.

Note that, also in the "acid polymerization and post-neutralization", additional monomer may be used with the acrylic acid as required, as with the foregoing polymerization method described in (6). Further, the condition (types, amount, etc.) of the additional monomers, the cross-linking monomer (internal-cross-linking agent), and the polymerization initiator are same as those described in (3), (4) and (5) above. Further, when the "acid polymerization and post-neutralization" is performed with a solvent, the concentration of the whole unsaturated monomer is not particularly limited; however, it is preferably adjusted to a small value, for example, 5-40% by mass, more preferably 10-30% by mass.

The polymerization is started with an aqueous solution kept at a low temperature, for example, 10-25° C.

In the "acid polymerization and post-neutralization", the cross-linked polymer resulting from the polymerization must be neutralized. An alkali metal hydroxide (sodium hydroxide, potassium hydroxide, lithium hydroxide, etc.), alkali metal carbonate (sodium carbonate, sodium bicarbonate etc.) or the like is used for the alkali metal compound, which induces neutralization of the acid group in the polymer so that a part of the cross-linked polymer is neutralized into alkali metallic salt. Otherwise, some kind of amine, such as ammonia, alkanol amine, or ammonium carbonate may be used. A sodium salt or a potassium salt is particularly preferable because (i) the sodium salt and potassium salt are easily obtained as commercial products, (ii) the sodium salt and potassium salt are harmless, and (iii) use of the sodium salt and/or potassium salt gives better property to the water-absorbent resin obtained and effects the other advantages. In this "acid polymerization and post-neutralization", it is preferable that 50-90 mol %, more preferably 60-80 mol % of the acid group in the cross-linked polymer be changed into alkali metallic salt resulting from neutralization reaction with the alkali metal compound. To carry out such neutralization of the cross-linked polymer produced by polymerization by using an alkali metal compound, the following method may be adopted. A gel polymer, which is obtained through polymerization with a solvent, is cut into 1 cm$^3$ or smaller pieces while pouring an aqueous solution of the alkali metallic compound into the gel.

Then, the gel is kneaded by a kneader or a meat chopper. To obtain the particulate water-absorbent resin of the present invention, the temperature in the neutralization is preferably 50-100° C., more preferably 60-90° C., and the first neutralization index (degree of neutralization for 200 particles; see Claim 1 of U.S. Pat. No. 6,187,872) is preferably even, specifically not more than 10.

(b) Method using a chain transfer agent (e.g., Manufacturing method 2)

In the manufacturing method of the particulate water-absorbent resin of the present invention, the polymerization may be performed by using a chain transfer agent, in addition to the unsaturated monomer, internal-cross-linking agent, and the polymerization initiator.

With the water-absorbent resin produced from the cross-linked polymer manufactured through this method, the ability as an absorbing agent and stability to urine are ensured for the particulate water-absorbing agent of the present invention.

The water-soluble chain transfer agent used for polymerization according to the present invention may be any agent soluble to the water or a water-soluble ethylene unsaturated monomer, such as thiol, thiol acid, the secondary alcohol, amine, hypophosphite or the like. More specifically, the chain transfer agent is selected from one kind or two kinds of: mercaptoethanol, mercaptopropanol, dodecylmercaptan, thioglycol, thiomalic acid, 3-mercaptopropionic acid, isopropanol, sodium hypophosphite, formic acid, and their salts. However, considering the property of the resulting polymer, most preferable is the hypophosphite, such as sodium hypophosphite.

The amount of the water-soluble chain transfer agent is determined depending on the type of the agent and/or the monomer concentration of the monomer aqueous solution, but is preferably 0.001-1 mol %, more preferably 0.005-0.3 mol %.

When the amount is less than 0.001 mol %, it is too much for the amount of the internal-cross-linking agent, thereby excessively increasing the cross-linking density, thus excessively decreasing the absorption capacity. Further, when the amount is more than 1 mol %, an excessive amount of water-soluble component becomes higher, thereby decreasing the stability.

(8) Drying

In general, the cross-linked polymer obtained by the foregoing polymerization method is a cross-linked polymer in a form of a water-containing gel. If necessary, the water-containing gel-form cross-linked polymer, which contains water in an amount of 10% to less than 70% is crushed and then dried. The drying is carried out at a temperature in a range of 60° C. to 250° C. in general, preferably in a range of 100° C. to 220° C., and more preferably in a range of 120° C. to 200° C. How long the drying is carried out (drying time) depends on how much surface area and moisture content the polymer has and which type of a dryer is used, so that the drying time is so set, as required, that the polymer will have a target moisture content after drying. Note that, in the present invention, only the dried cross-linked polymer is called a water-absorbent resin.

The moisture content of the water-absorbent resin used for the present invention is not particularly limited. However, it is preferable to control the moisture content so that the polymer is in a particle (powder) form and flowable even at room temperatures. That is, the water-absorbing agent has a moisture content generally in a range of 0.2 to 30% by mass, more preferably in a range of 0.3 to 15% by mass, further preferably in a range of 0.5 to 10% by mass. When the water content is more than this range, the fluidity of the water-absorbent resin decreases, thereby not only making the manufacturing difficult, but also making the crushing difficult. As a result, the desired particle size distribution may not be obtained. As the term is used herein, the "moisture content" is defined by the amount of water contained in the water-absorbent resin as measured by the proportion of the lost weight after drying in the mass of the water-absorbent resin before drying when 1 g of the water-absorbent resin is spread on a 52 mm aluminum cup and is dried for 3 hours at 180° C. As long as it is possible to attain the target moisture content, the drying is not particularly limited, and it is possible to adopt various methods. Specifically, the drying methods that can be adopted here are, for example, thermal drying, hot air drying, drying under reduced pressure, infrared drying, microwave drying, drying by azeotropy with a hydrophobic organic solvent, high-moisture drying in which a high temperature steam is used, and the like drying methods.

The shape of the water-absorbent resin used for the present invention, which is produced in the foregoing method, is not particularly limited as long as the resin can be treated as powder. Examples of shape include sphere, fiber, bar, substantially sphere, planular, irregular form, agglomerated form, porous structure etc. However, most preferable is irregular-shaped powder produced through pulverization.

(9) Pulverizing, classification, and control of particle size distribution, absorption capacity The water-absorbent resin produced through the manner of (8) above is processed into a specific particle (powder) size distribution so as to be completed as the particulate water-absorbing agent of the present invention.

In consideration of the characteristic of the particulate water-absorbent resin of the present invention, the diameter of the resin particle is set as follows. The mass average particle diameter is generally 150-600 μm, preferably 180-500 μm, more preferably 200-450 μm, further preferably 220-430 μm. Further, the percentage of particles less than 150 μm is generally 0-8% by mass, preferably 0-5% by mass, further preferably 0-3% by mass, still further preferably 0-1% by mass.

Further, in consideration of the characteristic of the particulate water-absorbing agent of the present invention, a desired bulk density (regulated by JIS K-3362-1998) of the water-absorbent resin is preferably in a range of 0.40-0.90 g/ml, more preferably in a range of 0.50-0.80 g/ml. Further, the percentage of 600-150 μm particles is 90-100%, more preferably 95-100%, further preferably 98-100% by mass with respect to the whole particle quantity. The logarithmic standard deviation ($\sigma\zeta$) of particle size distribution is preferably 0.20-0.50, more preferably 0.20-0.45, further preferably 0.20-0.40.

When the cross-linked polymer is manufactured through reversed suspension polymerization, the particle size may be adjusted by subjecting the particles to dispersion polymerization and dispersion drying. However, in general, when carrying out aqueous polymerization in particular, the particles are pulverized and classified after drying, and then mass average diameter of D50, and the amount of particles smaller than 150 μm, which are incompatible physical properties, is adjusted so as to obtain a specific particle size distribution. For example, if the specific particle size distribution is achieved by decreasing the diameter of the particles having mass average diameter of D50 to 400 μm or smaller and also reducing the amount of the fine particles having diameter less than 150 μm, the particles may be first classified into coarse particles and fine particles after drying by using a general classifying equipment such as a sieve. This process preferably removes coarse particles with a diameter of 5000 μm to 400 μm, more preferably of 2000 μm to 400 μm, further preferably of 1000 μm to 400 μm. Then, in the main adjustment process, it is preferable that the fine particles with a diameter less than 200 μm, more preferably less than 150 μm, are removed. The removed coarse particles may be discarded, but they are more likely to be pulverized again through the foregoing pulverizing process. Further, the removed fine particles are preferably subjected to the following "particle diameter enhancing process" to avoid the loss. The resulting water-absorbent resin thus produced with a specific particle size distribution through the pulverizing process is therefore constituted of irregularly-pulverized particles.

It should be noted that it is preferable that the water-absorbent resin obtained through the method of (8) above with the foregoing particle size distribution preferable has a centrifuge retention capacity, with respect to the physiological saline solution, not less than 30 g/g, preferably not less than 32-70 g/g, further preferably 35-65 g/g, still further preferably 40-60 g/g, before surface-cross-linking. The centrifuge retention capacity can be adjusted by changing the conditions in polymerization and/or in drying, for example, by changing the internal-cross-linking agent in polymerization. To obtain the particulate water-absorbent resin of the present invention, the water-absorbent resin is subjected to surface-cross-linking, which is described later. Accordingly, to produce the particulate water-absorbent resin of the present invention whose centrifuge retention capacity is not less than 27 g/g, the centrifuge retention capacity of the water-absorbent resin before surface-cross-linking must be at or more than 27 g/g. However, in the case of using an internal-cross-linking agent which causes an increase in centrifuge retention capacity of the water-absorbent resin itself by heating (see U.S. Pat. No. 5,389,722, No. 5,532,323), the centrifuge retention capacity may be less than 27 g/g.

(10) Particle Diameter Enhancing Process

The fine particle removed through the foregoing pulverizing, classification and the particle size distribution adjustment processes are reproduced as larger particles or as new particulate aggregation, which are still useful for the water-absorbent resin of the present invention. This particle diameter enhancing process for the fine particles is performed according to, for example, U.S. Pat. Nos. 6,228,930, 5,264,495, 4,950,692, 5,478,879, and EP Patent No. 844270. Note that, the recycled water-absorbent resin substantially has a porous structure.

The content of such a recycled water-absorbent resin produced by the foregoing process in the whole water-absorbent resin of the present invention is preferably 0-50% by mass, more preferably 5-40% by mass, further preferably 10-30% by mass. Since the recycled water-absorbent resin has a larger surface area than the original water-absorbent resin with same diameter, it ensures higher absorption rate when completed as a particulate water-absorbing agent product. That is, the recycled resin ensures better performance. This recycled water-absorbent resin whose particle diameter has been enhanced is first mixed with the water-absorbent resin having just been through the drying process (8) above, before subjected to pulverizing, classification and particle size distribution adjustment.

(11) Surface-cross-linking

As described in the "Manufacturing method 1" and "Manufacturing methods 2 through 4", the water-absorbent resin of the present invention is preferably includes, for example, a water-absorbent resin, which is first processed into a specific particle size distribution and specific absorption capacity, followed by surface-cross-linking. For example, the particulate water-absorbent resin of the present invention may be obtained by decreasing its centrifuge retention capacity (CRC) (to a value 95-50%, more preferably 90-60% of the original centrifuge retention capacity (CRC)) by the surface-cross-linking. It however should be noted that the degree of decrease in the centrifuge retention capacity (CRC) may be controlled by type/amount of the cross-linking agent, reaction temperature/time.

[Surface-cross-linking Agent]

The surface-cross-linking agent used for the foregoing surface-cross-linking process is required to have a function of necessarily forming ester bond with a carboxyl group. Without such a cross-linking agent, it is difficult not only to ensure the specific physical properties (centrifuge retention capacity, absorbency against pressure) but also to ensure safety of residual cross-linking agent. This is because other general cross-linking agents are generally not as safe as the specific cross-linking agent (preferable example are (a) multivalent alcohol compounds, (b) alkylene carbonate compounds, (c) oxetane compounds, or (d) amino alcohol compounds) which form ester bond with a carboxyl group.

A possible example of the surface-cross-linking agent for causing ester bond (preferably dehydrate enter bond) to a functional group (carboxyl group) of the polycarboxylic acid water-absorbent resin may be one made of multivalent alcohol or amino alcohol whose molecules contain hydroxyl groups, or one producing a hydroxyl group in response to ring-opening of alkylene carbonate, oxazolidinone, oxetane etc.

Examples of the surface-cross-linking agent are polyvalent alcohol compounds such as mono-, di-, tri-, or polyethyleneglycol, monopropyleneglycol, 1,3-propanediol, 1-methyl-1,3-propanediol, 2-methyl-1,3-propanediol, dipropyleneglycol, 2,3,4-trimethyl-1,3-pentanediol, polypropyleneglycol, glycerin, polyglycerin, 2-butene-1,4-diol, 1,4-butanediol, 1,3-butanediol, 1,5-pentanediol, 1,6-hexanediol, meso-erythritol, D-sorbitol, and 1,2-cyclohexanedimethanol; (ii) oxazolidinone compounds (U.S. Pat. No. 6,559,239) such as N-acyloxazolidine and 2-oxazolidine; (iii) alkylen carbonate compounds (U.S. Pat. No. 5,409,771) such as 1,3-dioxolan-2-on (also referred to as "ethylene carbonate"), 4-methyl-1,3-dioxolan-2-on, 4,5-dimethyl-1,3-dioxolan-2-on, 4,4-dimethyl-1,3-dioxolan-2-on, 4-ethyl-1,3-dioxolan-2-on, 4-hydroxymethyl-1,3-dioxolan-2-on, 1,3-dioxane-2-on, 4-methyl-1,3-dioxane-2-on, 4,6-dimethyl-1,3-dioxane-2-on, and 1,3-dioxespan-2-on; (iv) oxetane compounds (e.g., 3-ethyl-3-hydroxymethyloxetane) and cyclic urea compounds (e.g., 2-imidazolidinone) (U.S. Patent No. 2002/0072471); and (v) aminoalcohol compounds such as ethanolamine, diethanolamine, and triethanolamine. These examples may be used either alone or in combination.

To obtain the particular odor-suppressing effect of the present invention as well as the surface-cross-linking function, the surface-cross-linking agent is preferably made of at least one raw material selected from the group of: polyhydroxy alcohol or amino alcohol with 3-6 carbons and having molecules each containing 2-3 hydroxyl groups, alkylene carbonate with 3-5 carbons, and a oxetane compound with 2-10 carbons. A further preferable surface-cross-linking agent is made of at least one raw material selected from the group of: glycerin, 1,3-propanediol, polyethylene glycol, ethylene carbonate, 3-ethyl-3-hydroxyl methyl oxetane and ethanol amine.

The amount of the surface-cross-linking agent is determined depending on the type and/or combination of the compounds used for the surface-cross-linking agent. However, the preferable amount is in a range of 0.001-10% by mass, more preferably 0.01-5% by mass, with respect to the whole water-absorbent resin.

Further, the surface-cross-linking agent may include "other cross-linking agents". Examples of the "other cross-linking agent" are as follows: (i) epoxy compounds such as ethyleneglycoldiglycidilether and glycidol; (ii) polyvalent amino compounds such as ethylenediamine, diethylenetriamine, triethylenetetramine, tetraethylenepentamine, pentaethylenehexamine, polyethyleneimine, and polyamide-polyamine; (iii) haloepoxy compounds such as epichlorohydrin, epibromhydrin, and α-methylepichlorohydrin; and (iv) condensates of the polyvalent amine compounds and the haloepoxy compounds. The "other cross-linking agents" may make up 0 to 10, preferably 0 to 5, and more preferably 0 to 1, % by mass of a total percent by mass of the total surface-cross-linking agent.

[Addition of Surface-cross-linking Agent and Heating Process]

In performing the surface-cross-linking, it is preferable to use water. In this case, an amount of the water to be used depends on how much moisture content of the water-absorbent resin to be used has. In general, with respect the whole water-absorbent resin, the amount of the water to be used is preferably in a range of 0.5-20% by mass, more preferably in a range of 0.5-10% by mass.

It is possible to use a hydrophilic organic solvent in addition to water and the surface-cross-linking agent; however, the amount should be as small as possible to avoid occurrence of odor from the resulting particulate water-absorbing agent. Specifically, the amount of the hydrophilic organic solvent is in a range of 0-10% by mass, preferably in a range of 0-5% by mass, and more preferably in a range of 0-3% by mass, particularly preferably 0% by mass (substantially not used) with respect to the whole water-absorbent resin. The hydrophilic organic solvent used in the present invention means an organic solvent, at least 1 g, preferably not less than 10 g, more preferably not less than 100 g, of which is dissolved into 100 g water at room temperature. It is also preferable that the boiling point of the hydrophilic organic solvent be at or lower than 150° C.

Further, it is also allowable to use various acids such as an organic acids (lactic acid, citric acid, p-toluenesulfonic acid etc.) or an inorganic acid (phosphoric acid, sulfuric acid, sulfurous acid etc.), various bases such as caustic soda, carbonic acid soda etc., or various multivalent metals such as aluminium sulfate, in addition to the surface-cross-linking agent. However, the amount of them should be adjusted so that the extent of odor of the resulting resin does not exceed the allowable level for the particulate water-absorbent resin of the present invention. Specifically, the amount is preferably in a range of 0-10 weight %, more preferably in a range of 0-5 weight %, further preferably in a range of 0-1 weight %.

In the present invention, the following mixing method is preferable: in advance, the surface-cross-linking agent is mixed with water and/or the hydrophilic organic solvent, and the mixture is dropped, more preferably sprayed, into the water-absorbent resin. An average diameter of liquid droplets to be sprayed is preferably 0.1 to 300 μm, and more preferably 0.1 to 200 μm.

As to a mixing apparatus for use in mixing the water-absorbent resin, the surface-cross-linking agent, and water or the hydrophilic organic solvent, it is preferable that the mixing apparatus has a large mixing power in order that these compounds are mixed uniformly and thoroughly. Examples of mixing apparatuses that can be preferably used as the mixing apparatus are: a cylindrical mixer, double-wall conical mixer, a high-speed stirring mixer, a V-shaped mixer, a ribbon blender, a screw mixer, a double-arm kneader, a crush-type kneader, a rotary mixer, an air current mixer, a turbulizer, batch-type Lödige mixer, continuous Lödige mixer, and the like apparatuses.

After mixing the surface-cross-linking agent with the water-absorbent resin, it is preferable that the water-absorbent resin is heated. Conditions of the heating are: water-absorbent resin or a heating medium used to perform the heating preferably has a temperature in a range of 120° C. to 250° C., more preferably in a range of 150° C. to 250° C.; and heating period is preferably in a range of one minute to two hours. Examples of appropriate combinations of the heating temperature and heating period are: (a) 180° C. for 0.1 to 1.5 hours, and (b) 200° C. for 0.1 to one hours.

The device for carrying out heating is not particularly limited, and may be any devices uniformly propagates heat to the mixture of the surface-cross-linking agent and the water-absorbent resin. However, the heating device preferably has a large mixing device, which ensures even heating treatment. Examples of the heating device include various dryers or heaters, such as a belt-type device, a channel mixing device, a screw-type device, a rotation-type device, a disk-type device, a kneader, a flow-type device, an airflow-type device, an infrared device, or an electron ray device.

[Exposure to Airflow]

A preferable manufacturing method to be adopted in the present invention includes an airflow exposure process. More specifically, after or while the water-absorbent resin having been mixed with a surface-cross-linking agent is heated, it is preferably exposed to airflow. This airflow exposure process is performed to circulate/replace the gas inside the processing device after or while the water-absorbent resin having been mixed with a surface-cross-linking agent is heated or subjected to other treatments. The high temperature heat treatment generates a volatile component which causes odor, and the airflow exposure process serves to remove the volatile component. The gas to which the resin is exposed may be water vapor, air, nitrogen, or a mixture of them. The amount of the gas is determined according to the circumstances; however it generally is 0.001-100 $m^3$/hr, preferably 0.01-10 $m^3$/hr per unit volume 1 $m^3$ of the heating device or other device in which the water-absorbent resin or the particulate water-absorbing agent exists. To express this range in the linear velocity of the airflow, the linear velocity is preferably in a range of 0.01-100 m/s, more preferably in a range of 0.1-50 m/s. Further, the exposure time is preferably in a range of 1-120 minutes, more preferably 10-90 minutes. The airflow may be generated by ventilation or suction. Further, the change in pressure due to the ventilation/suction is preferably within 10%, more preferably within 1%.

When the exposure to airflow is carried out at the stage of heating the water-absorbent resin having been mixed with a surface-cross-linking agent, a dryer/heater having a gas supplying device or a gas discharging device is preferably used. It is also preferable that the replacement of gas (water vapor, air, nitrogen, or a mixture of them) in the dryer/heater does not take too long, because it may excessively decrease the temperature of the device from the default value (preferably in a range of 120° C.-250° C.). If the temperature excessively drops, the energy supply cannot be ensured.

When the exposure to airflow is carried out after the heating treatment, it is preferable to aerate the cooling device, the transfer line, and the tube by which the water-absorbent resin having been mixed with a surface-cross-linking agent is cooled and transferred. It is allowable to heat or cool the gas; however, in order to facilitate evaporation of the volatile component, which causes odor, from the water-absorbent resin or the particulate water-absorbing agent, the temperature of the gas is preferably kept at not less than 50° C., more preferably not less than 60° C., further preferably not less than 70° C. Note that, when the temperature of airflow to which the resin is exposed is below 50° C., removal of the volatile component cannot be ensured. Further, since the exposure is performed after the heating treatment, the temperature has to be set lower than 120° C., the heating temperature.

Further, this airflow exposure process at a predetermined temperature offers not only an effect of reduction of odor, but also an effect of removal of ethylene glycol which is generated during the high-temperature heating when using an alkylene carbonate compound, 1, 3 dioxolane-2-on in particular, as a surface-cross-linking agent.

The ethylene glycol is suspected to harm human body in some way, and therefore should be removed or at least reduced as much as possible at this stage. The harm of the ethylene glycol is more specifically described later.

Apart from the foregoing airflow exposure process at a predetermined temperature, another possible method of removing odor, ethylene glycol etc. is cleaning of the water-absorbent resin or the particulate water-absorbing agent having been subjected to surface-cross-linking. For example, the resin or the agent may be washed by a solvent having a low boiling point, so as to reduce or remove a constituent causing odor. To be more specific, the solvent preferably has a boiling point of not less than 0° C. but lower than 70° C., more preferably has a boiling point of not less than 30° C. but lower than 50° C. Acetone, dimethylether, methylene chloride are particularly preferable. Further, since the ethylene glycol is soluble in water, it is possible to use water; however the amount of water is limited because an excessive amount of water may cause swelling of the water-absorbent resin. The resin thus washed by a solvent may have odor derived from the solvent. To avoid this, the solvent needs to be removed from the resin until the content of the alcohol volatile component falls within a predetermined allowable range. This removal of alcohol volatile component may be carried out, for example, by subjecting the water-absorbent resin or the particulate water-absorbing agent to hot-air drying. The hot-air drying must be stopped before the performance of the water-absorbent resin or the particulate water-absorbing agent deteriorates.

(12) Agglomeration

To produce the particulate water-absorbing agent of the present invention, the water-absorbent resin having been subjected to surface-cross-linking is then mixed with water so as to be converted into agglomeration of certain particle size distribution, if required. The water to be added may contain a chelating agent, a plant extract, an antibacterial agent, a water-soluble polymer, inorganic salt etc. so that the concentration of the resulting aqueous solution becomes in a range of 0.001-50% by mass. A suitable agglomeration method and recommended processes are described in Japanese Unexamined Patent Publication Tokugan 2004-211856.

(13) Addition of Chelating Agent

The particulate water-absorbing agent of the present invention may contain a chelating agent, particularly a multivalent carboxylic acid and the salt thereof.

Especially, according to the foregoing "Manufacturing method 4", the particulate water-absorbing agent of the present invention is manufactured as follows. An unsaturated monomer aqueous solution, which contains a non-neutralized acrylic acid and/or the salt thereof as a main component of the monomer, is subjected to cross-link-polymerizing in the presence of an internal cross-linking agent; and the particle size distribution of the water-absorbent resin is then adjusted. The resulting cross-linked polymer having a specific absorption capacity and a specific particle size distribution is subjected to surface-cross-linking. A chelating agent is added during the polymerization, or before, after or during the surface-cross-linking. The particulate water-absorbing agent of the present invention may thus contain a chelating agent by adopting the "manufacturing method 4".

Preferable example of the chelating agent to be contained in the particulate water-absorbing agent of the present invention is one having a high ion-blocking function or a high chelating function with respect to Fe or Cu. Specifically, the chelating agent preferably has a stability constant of not less than 10, more preferably not less than 20 with respect to Fe ion. A further preferable chelating agent is one containing three or more of amino multivalent carboxylic acids and the salt thereof, more preferably three or more of amino carboxylic groups and the salt thereof.

Specific examples of the polyvalent carboxylic acids are diethylenetriamine pentaacetic acid, triethylenetetraamine hexaacetic acid, cyclohexane-1,2-diamine tetraacetic acid, N-hydroxyethylethylenediamine triacetic acid, ethyleneglycoldiethyletherdiamine tetraacetic acid, ethylenediamine tetrapropionic acid, N-alkyl-N'-carboxymethyl asparagine acid, N-alkenyl-N'-carboxymethyl asparagine acid, alkali metal salts thereof, alkaline earth metal salts thereof, and ammonium salts thereof or amine salts thereof. Particularly, diethylenetriamine pentaacetic acid, triethylenetetraamine hexaacetic acid, N-hydroxyethylethylenediamine triacetic acid, and salts thereof are most preferable.

In the present invention, the amount of chelating agent, particularly the amount of amino multivalent carboxylic acid should be small, specifically, in a range of 0.00001-10 weight %, more preferably in a range of 0.0001-1 weight % with respect to 100 weight % of the water-absorbent resin. When the amount is more than 10 weight %, the effect is no longer proportional to the amount, that is, it only takes more cost; in addition, it may cause a decrease in absorbing agent ability. Further, when the amount is less than 0.00001 weight %, the required function of the chelating agent would not be brought out.

(14) Other Additives

Apart from the chelating agent, the present invention also allows use of a little amount of various additives, such as (A) plant extract, (B) organic multivalent metallic salt, (C) inorganic particles (including (D) composite hydrous oxide)), (E) reductive substance, so as to give various additional functions to the particulate water-absorbing agent of the present invention.

The respective amounts of the additives (A) through (E) and (F) are determined depending on the objective or the desired function; however, each content is generally 0-10 parts by weight, preferably 0.001-5 parts by weight, more preferably 0.002-3 parts by weight. When the content is less than 0.001 parts by weight, the desired effect or function cannot be ensured. On the other hand, when the content is more than 10 parts by weight, the effect is no longer proportional to the amount, or the absorption ability decreases.

(A) Plant Extract

The particulate water-absorbing agent of the present invention may contain a plant extract within the foregoing range to have a deodorant property. A preferable plant extract for the present invention is at least one compound selected from the group of: polyphenol, flavone or the relatives, and caffeine; or at least one compound selected from the group of: tannin, tannic acid, galla, nutgall, and gallic acid. Other preferable plant extracts can be found in U.S. Pat. No. 6,469,080, WO2002/423479, or International Patent Application PCT 2003/JP6751.

(B) Multivalent Metallic Salt

The particulate water-absorbing agent according to the present invention may contain a polyvalent metal salt, particularly a polyvalent metal salt of organic acid, within the foregoing range, so as to improve powder fluidity or to prevent caking due to moisture absorption.

Specific examples of the multivalent metallic salt and the mixing method can be found in International Patent Applications PCT/JP2004/1355, PCT/JP2004/1007, PCT/JP2004/1294, or PCT/JP2004/9242. The present invention uses an organic metallic salt which contains 7 or more carbons per molecule (PCT/JP2004/1355), and particularly prefers one constituted of a metallic salt other than an alkali metallic salt, such as fatty acid, petroleum acid, or a polymer acid.

(C) Inorganic Particles

The particulate water-absorbing agent of the present invention may contain inorganic particles, particularly water-insoluble inorganic particles, so as to have a function of preventing caking due to moisture absorption. The inorganic particles used for the present invention may be a metal oxide such as silicon dioxide, titanium oxide etc., silicic acid (salt) such as natural zeolite, artificial zeolite etc., kaolin, talc, clay, bentonite etc. Among these, the silicon dioxide and the silicic acid (salt) are particularly preferable, especially one with an average particle diameter of 0.001-200 μm, which is measured by a Coulter counter.

(D) Composite Hydrous Oxide

The particulate water-absorbing agent of the present invention has an excellent "fluidity after moisture absorption (fluidity after the water-absorbent resin or the particulate water-absorbing agent absorbs moisture)". The particulate water-absorbing agent of the present invention may further contain a composite hydrous oxide including zinc and silicon, or a composite hydrous oxide including zinc and aluminium (see Japanese Unexamined Patent Publication Tokugan 2003-

280373, and PCT/JP2004/10896). With such a composite hydrous oxide, the particulate water-absorbing agent is given an excellent deodorant property.

(E) Reductive Substance

The water-absorbing agent of the present invention preferably contains a reductive substance, particularly an inorganic reductive substance, more particularly a reductive substance containing sulfur or oxygen. A suitable example of the reductive substance is a compound included sulfur or oxygen, more preferably sulfite or hydrogen-sulfite, which are disclosed in U.S. Pat. No. 4,863,989, or in U.S. Pat. No. 4,863,989.

(F) Others

As long as the particular characteristic/property is ensured, the particulate water-absorbing agent of the present invention may contain any other additives, such as an antibacterial agent, water-insoluble polymer, water, organic particles etc.

(15) Particulate Water-absorbing Agent of the Present Invention

The particulate water-absorbing agent manufactured through the foregoing method or Manufacturing method 1, 2, 3 or 4 is a brand-new particulate water-absorbing agent having a new performance that has never been achieved by the conventional agents. That is, the particulate water-absorbing agent of the present invention is designed/made based on the five specific physical properties in accordance with new findings ((1)a desired surface-cross-linking agent, desires physical property, and allowable level of odor are incompatible, 2) a desired average particle diameter and allowable amount of dust-size particle are incompatible, 3) the five physical properties are important factors for the water-absorbent agent used as an absorbent structure of disposal diaper or the like). The present invention thus provides a practically ideal particulate absorbent structure product satisfying the five specific physical properties.

The particulate water-absorbing agent (first water-absorbing agent) according to the present invention contains, as a main component, a particulate polycarboxylic acid water-absorbent resin having a surface cross-linked by a surface-cross-linking agent which forms ester bond with a carboxyl group, the particulate water-absorbing agent satisfying following conditions:

(a) a centrifuge retention capacity (CRC) for a physiological saline solution being not less than 27 g/g;

(b) an absorbency against pressure (AAP) of 4.8 kPa for the physiological saline solution being not less than 20 g/g;

(c) a mass average particle diameter (D50) being 200-450 μm;

(d) an amount of particles smaller than 150 μm in the particulate water-absorbing agent being 0-5% by mass;

(e) a logarithmic standard deviation ($\sigma\zeta$) of particle size distribution being 0.20-0.40; and (f) a content of an alcohol volatile substance evaporated from the particulate water-absorbing agent being 0-10 ppm, the content being measured by a gas detecting tube as an atmosphere concentration.

The following more specifically explains the particulate water-absorbing agent of the present invention.

[Alcohol Volatile Substance]

The alcohol volatile substance designates an amount (atmosphere concentration measured by a gas detector) of an alcohol volatile substance detected by the measurement method defined in "Examples" of this specification, and particularly designates a volatile component measured by an alcohol detection tube (a methanol gas detection tube in particular).

As explained, the alcohol volatile substance designates a volatile component measured by an alcohol detection tube, particularly by a methanol gas detection tube, and therefore it does not necessarily means alcohol. That is, it indicates a gross amount of volatile components measured in alcohol-basis conversion. Accordingly, other volatile substances than alcohol, e.g., the acetic acid, the propionic acid, the residual monomer (acrylic acid) may also be detected as the alcohol volatile substance.

The inventors of the present invention have studied the deodorant property (for example, by the use of deodorant agent) of the water-absorbent resin (water-absorbing agent) as its additional function, and found an unexpected fact that a water-absorbent resin itself generates a characteristic odor after swelling, which has been actually decreasing the deodorant property of the absorbing agent when used as a product such as disposal diaper. From this viewpoint, the inventors carried out further examination of odor of the water-absorbent resin, and the deodorant property when the resin is used as disposal diaper or the like, and found that the odor of the water-absorbent resin and the deodorant property when the resin is used as disposal diaper are highly related to the atmosphere concentration, which is detected by an alcohol detection tube. The inventor studied this new parameter, and found its critical range, thereby completing the present invention.

The content of the (f) alcohol volatile substance of the particulate water-absorbing agent of the present invention is generally 0-10 ppm, preferably 0-8 ppm, more preferably 0-5 ppm, further preferably 0 ppm (undetectable). When the content falls outside this range, the volatilization of odorant increases, and the effect of the present invention is not ensured.

[Absorption Capacity]

The inventors of the present invention found that, in the conventional absorbing agent, the preferable surface-cross-linking agent (the cross-linking agent inducing ester bond with a carboxyl group), the desired physical properties (high absorbency against pressure, high centrifuge retention capacity etc.), and the odor (deodorant property) are incompatible. The inventors further found that overcoming this problem creates a water absorbent article (disposal diaper etc.) ensuring high physical properties.

More specifically, the (a) centrifuge retention capacity (CRC) for the physiological saline solution of the particulate water-absorbing agent according to the present invention is generally not less than 27 g/g, preferably not less than 28 g/g, not less than 29 g/g, not less than 30 g/g, not less than 33 g/g, or not less than 36 g/g. When the centrifuge retention capacity is less than 27 g/g, the high physical properties of the resin may not be ensured when used as disposal diaper or the like. The upper limit of the CRC is not limited, but when the value exceeds 60 g/g, there may be some difficulties in manufacturing and may increase the cost.

The (b) absorbency against pressure (AAP) of the particulate water-absorbing agent of the present invention under 4.8 kPa is generally not less than 20 g/g, preferably not less than 22 g/g, more preferably not less than 24 g/g, further preferably not less than 26 g/g. When the absorbency against pressure is less than 20 g/g, the high physical properties of the resin may not be ensured when used as disposal diaper or the like. The upper limit of the AAP is not limited, but when the value exceeds 35 g/g, there may be some difficulties in manufacturing and may increase the cost.

[Particle Size Distribution]

Further, in addition to the specific surface-cross-linking agent, the specific physical properties and the odor; the inventors also found the average particle diameter and the dust-size particle amount of the water-absorbing agent (water-absorbent resin) as important factors for a water absorbent article (such as disposal diaper) ensuring high physical properties. Then, in studying these factors, the inventors found that the average particle diameter and the dust-size particle amount are also incompatible, and overcoming this problem achieves a water absorbent article (such as water diaper) ensuring high physical properties.

Specifically, in the particulate water-absorbing agent of the present invention, the (c) mass average particle diameter (D50) is generally 200-450 µm, preferably 220-430 µm, more preferably 250-400 µm. Further, the particulate water-absorbing agent of the present invention contains particles less than 150 µm in an amount of 0-5% by mass, preferably 0-3% by mass, more preferably 0-1% by mass. Furthermore, the (e) logarithmic standard deviation ($\sigma\zeta$) of particle size distribution is generally set to 0.20-0.40, preferably 0.20-0.38, more preferably 0.20-0.35.

Particle size distribution is adjusted as follows. First the particles are processed into a certain size before being subjected to surface-cross-linking, and then, after the surface-cross-linking, the particles are subjected to pulverizing, classification, and agglomeration, thereby obtaining particles of certain size. Further, when the particle size falls outside the range, the particular effect of the present invention is not ensured when the resin is used as an absorbent product, such as disposal diaper.

[Content of Residual Ethylene Glycol]

The content (determined by HPLC) of the residual ethylene glycol in the particulate water-absorbing agent of the present invention is generally 0-40 ppm, preferably 0-30 ppm, more preferably 0-20 ppm, further preferably 0 ppm (undetectable). When the content falls outside this range, it may result in not only odor but also some kind of harm to human body.

The inventors of the present invention found a fact that ethylene glycol is detected even from a water-absorbent resin not using ethylene glycol as a monomer or as a cross-linking agent, and also found a safety problem in connection with the ethylene glycol. Then, the inventors examined the origin of the ethylene glycol, and found that the detected ethylene glycol is impurity, or, in many cases, decomposition product of the surface cross-agent used for the raw material (particularly, ethylene glycol derivative, such as ethylene carbonate or polyethylene glycol). Especially, if alkylene carbonate (particularly, ethylene carbonate) is used as a surface-cross-linking agent so as to increase the physical property (particularly, liquid-permeability under pressure or absorbency against pressure), it is necessary to use a large amount of cross-linking agent and to carry out a reaction process at high temperature. Thus, even when no ethylene glycol is used for the raw material, or even when alkylene carbonate such as ethylene carbonate is completely free from ethylene glycol or ethylene glycol impurity, the water-absorbent resin completed as a commodity contain ethylene glycol as a by-product.

In view of this, the particulate water-absorbing agent of the present invention is preferably manufactured as follows. First, the water-absorbent resin is prepared without using ethylene glycol, and also the ethylene glycol or ethylene glycol impurity contained in the ethylene carbonate or polyethylene glycol are reduced (until the purity becomes 98% or greater, preferably 99% or greater, more preferably 99.9% or greater). Then, when the water-absorbent resin is processed to be a product, the ethylene glycol by-product is removed, more preferably washed or evaporated. To be more specific, the resin is exposed to airflow at a temperature of 60° C. or at a higher temperature.

In this way, the present invention does not only ensure high purity of the raw material so as to reduce the content of ethylene glycol in the particulate water-absorbing agent, but also overcome the problem of by-product of ethylene glycol which is produced even in the resin made of a highly-pure raw material (especially ethylene carbonate) which is substantially free from ethylene glycol or ethylene glycol impurities. The water-absorbent resin of the present invention therefore has a high physical property.

The particulate water-absorbing agent (second water-absorbing agent) according to the present invention contains, as a main component, a particulate polycarboxylic acid water-absorbent resin having a surface cross-linked by a surface-cross-linking agent which contains alkylene carbonate and forms ester bond with a carboxyl group, the particulate water-absorbing agent satisfying following conditions:

(a) a centrifuge retention capacity (CRC) for a physiological saline solution being not less than 27 g/g;

(b) an absorbency against pressure (AAP) of 4.8 kPa for the physiological saline solution being not less than 20 g/g;

(c) a mass average particle diameter (D50) being 200-450 µm;

(d) an amount of particles smaller than 150 µm in the particulate water-absorbing agent being 0-5% by mass;

(e) a logarithmic standard deviation ($\sigma\zeta$) of particle size distribution being 0.20-0.40; and (g) a content (determined by HPLC) of residual ethylene glycol in the particulate water-absorbing agent being 0-40 ppm.

The second water-absorbing agent preferably further satisfies a (f) range of content of alcohol volatile substance of 0-10 ppm, satisfies the physical properties (h) through (j) below, and contains the additives below.

The inventors of the present invention found that, when a water-absorbent resin is subjected to surface-cross-linking using alkylene carbonate (particularly, ethylene carbonate) as a surface cross-linking agent so as to increase the physical property (particularly, liquid-permeability under pressure or absorbency against pressure), the resulting water-absorbent resin product contains ethylene glycol as a by-product even when no ethylene glycol is used for the raw material, or even when alkylene carbonate such as ethylene carbonate is completely free from ethylene glycol or ethylene glycol impurity. Conventionally, the by-product ethylene glycol causes various problems such as a safety problem, but the present invention provides a new absorbing agent immune to such problems.

A manufacturing method of the particulate water-absorbing agent according to the present invention comprises the steps of:

(i) subjecting an aqueous solution of an unsaturated monomer, which contains a non-neutralized acrylic acid and/or its salt as a main component, to cross-link-polymerizing in a presence of an internal-cross-linking agent, so as to obtain a cross-linked polymer;

(ii) drying the cross-linked polymer, and adjusting a particle size distribution of the cross-linked polymer, so as to obtain a water-absorbent resin satisfying following conditions:

(a) a centrifuge retention capacity (CRC) for a physiological saline solution being not less than 30 g/g;

(b) a mass average particle diameter (D50) being 200-450 µm;

(c) an amount of particles smaller than 150 µm in the particulate water-absorbent resin being 0-8% by mass;

(d) a logarithmic standard deviation ($\sigma\zeta$) of particle size distribution being 0.20-0.50;

(iii) heating a vicinity of a surface of the water-absorbent resin after adding a cross-linking agent forming ester bond; and (iv) exposing the water-absorbent resin during or after the heating to airflow at or higher than 60° C.

The manufacturing method preferably uses (particularly for the second water-absorbing agent) a surface-cross-linking agent which contains alkylene carbonate and forms ester bond.

(16) Other Characteristics of the Particulate Water-absorbing Agent of the Present Invention.

[Second Component]

The particulate water-absorbing agent of the present invention further contains, in addition to the water-absorbent resin (main component), an alcohol compound (except for ethylene glycol) selected from: aminoalcohol, alkylene carbonate, and multivalent alcohol. Note that, since alkylene carbonate is an alcohol derivate (for example, ethylene carbonate is derived from ethylene glycol and carbon dioxide), the definition of alcohol compound of the present invention includes alkylene carbonate regardless of whether or not it contains a hydroxyl group.

Addition of the alcoholic compound improves fixation of the adsorbing agent into the disposal diaper or the like, prevents dust issue of fine particles included in the absorbing agent, and improves absorption rate. The content of the alcoholic compound is generally 10-10000 ppm, preferably 20-5000 ppm, more preferably 30-3000 ppm, with respect to the whole weight of the water-absorbent resin. The alcoholic compound is added separately, or may otherwise be added as a surface-cross-linking agent, which is left a certain amount. However, it should be noted that, even the compound falls within the range, an excessive content (outside the foregoing range (f)) of alcohol volatile substance may cause odor when the resin particles are swollen; therefore the content of alcohol volatile substance is preferably within the foregoing range.

[Third Component]

The particulate water-absorbing agent of the present invention further contains, in addition to the water-absorbent resin (main component), a trace component selected from: chelating agent, deodorant agent, multivalent metallic salt, and inorganic particles.

[Surface Cross-linking Agent]

The foregoing surface-cross-linking agent forming ester bond is preferably constituted of at least one compound selected from the group consisting of: glycerin, 1,3-propanediol, ethylene carbonate, 3-ethyl-3-hydroxyl methyl oxetane and ethanol amine. The higher purity the better, specifically, it is preferably not less than 93%, more preferably not less than 95%, further preferably not less than 97%.

[Sulfuric Volatile Substance]

The (h) content (mass quantity, also expressed as atmosphere concentration measured by a gas detector (defined in the specification)) of the sulfuric volatile substance is generally 0-10 ppm, preferably 0-5 ppm, more preferably 0-2 ppm, further preferably 0-0.3 ppm, still further preferably 0 ppm (undetectable).

The content of sulfuric volatile substance more than 10 ppm is not preferable, as it results in a critic decrease in deodorant property. The sulfuric volatile substance is assumably derived from decomposition product or impurities of the volatile sulfuric compound (e.g., persulfate, bisulfite), which is the raw material of the water-absorbing agent. Therefore, the problem will be solved by completely excluding the sulfuric volatile substance from the absorbing agent, or by reducing the impurities of sulfuric volatile substance (until the purity becomes 99.99% or greater, for example).

[Residual Monomer]

(i) A total amount (determined by HPLC) of acrylic acid, acetic acid and propionic acid of the particulate water-absorbing agent of the present invention is 0-1000 ppm, preferably 0-500 ppm, more preferably 0-300 ppm, further preferably 0-200 ppm, particularly preferably 0-1000 ppm. A content more than 500 ppm is not desired, as it critically decreases the deodorant property. In view of this, the polymerization is preferably performed by using the foregoing highly-pure acrylic acid, for example.

[White Index]

The (j) white index of the particulate water-absorbing agent of the present invention is expressed by a luminance index L and chromaticness indices a and b, all measured by a Hunter calorimeter. Preferably, the luminance index L is 80 or greater, a is −3 to 3, and b is −5 to 15, more preferably L is 83 or greater, a is −2.5 to 2.5, and b is −3 to 13, further preferably L is 85 or greater, a is −2 to 2, and b is 0 to 10.

When the white index of the water-absorbing agent falls outside the foregoing range, the agent will be not suitable for an absorbent article product such as paper diaper, particularly when used with high content. In this view, it is preferable that the polymerization is carried out with highly-pure acrylic acid.

[600-150 μm Particles]

Further, the particulate water-absorbing agent of the present invention preferably has a bulk density (regulated by JIS K-3362) of 0.40-0.90 g/ml, more preferably 0.50-0.80 g/ml. Further, it is also preferable that the percentage of 600-150 μm particles is 80-100%, more preferably 85-100%, further preferably 90-100% by mass with respect to the whole particle quantity. The water-absorbing agent not satisfying this range is not suitable as a water absorbent article product (e.g., disposal diaper), and has a poor deodorant property. In this view, the present invention performs the foregoing adjustment in particle size distribution before the surface-cross-linking, and agglomeration/classification of particle after the surface-cross-linking.

[Vortex Absorption Rate]

The absorption rate of the particulate water-absorbing agent of the present invention is preferably in a range of, when defined as a Vortex absorption rate for physiological saline solution, not more than 60 seconds, more preferably 1-55 seconds, further preferably 2-50 seconds. When the absorption rate exceeds 60 seconds, the particulate water-absorbing agent or the water-absorbent resin may not have sufficient absorption ability when used as an absorbent structure of disposal diaper or the like.

[Amount of Extractables, Increased Extractables by Deterioration, and Increased Ratio of Extractables by Deterioration]

The amount of extractables per hour in the particulate water-absorbing agent of the present invention must be not more than 40% by mass, preferably 0.1-30% by mass, more preferably 0.2-25% by mass, further preferably 0.3-20% by mass, particularly preferable 0.4-15% by mass, most preferably 0.5-10% by mass. When the amount of extractables exceeds the foregoing range, the extractables are dissolved into the absorbent structure when the water-absorbing agent absorbs water. This may block diffusion of the liquid (blood, urine) into the absorbent structure. As to the lower limit, it is difficult to create a water-absorbing agent within an allowable cost range if the content of soluble matter falls below the foregoing lower limit.

The increased extractables by deterioration in the particulate water-absorbing agent of the present invention is generally 0-15% by mass, preferably 0-10% by mass, further preferably 0-8% by mass, particularly preferably 0-5% by mass. When the increased extractables by deterioration exceeds 15% by mass, stability of water-absorbent resin with respect to urine becomes insufficient, and the structure of resin as a cross-linked polymer will deteriorate after a certain time period. This may excessively decrease the absorption ability of the resin.

The increased ratio of extractables by deterioration in the particulate water-absorbing agent of the present invention is generally 1-4 times, preferably 1-2 times, more preferably 1-1.5 times. When the increased ratio of extractables by deterioration exceeds the upper limit (4 times), stability of water-absorbent resin with respect to urine becomes insufficient, and the structure of resin as a cross-linked polymer will deteriorate after a certain time period. This may excessively decrease the absorption ability of the resin. The measurement methods for these parameters are described in Japanese Unexamined Patent Publication Tokugan 2004-96083.

(17) Absorbent Structure and Absorbent Article

The usage of the particulate water-absorbing agent of the present invention is not particularly limited; however, the particulate water-absorbing agent is preferably used as an absorbent structure or an absorbent article. The particulate water-absorbing agent ensures superior absorption ability especially as a high-content disposal diaper (a single diaper sheet contain a large amount of water-absorbent resin), which has conventionally been having the odor problem.

The absorbent structure of the present invention is made of the foregoing particulate water-absorbing agent. It should be noted that an absorbent structure according to the present invention means an absorbing raw material (in the form of a sheet etc.) constituted of the particulate water-absorbing agent and, if required, a hydrophilic fiber. If the hydrophilic fiber is not used, the particulate water-absorbing agent is fixed on a sheet or a nonwoven fabric.

The absorbent structure of the present invention contains a large amount (high core content) of particulate water-absorbing agent with respect to the total amount of the particulate water-absorbing agent and the hydrophilic fiber, that is 30-100% by mass, preferably 40-100% by mass, more preferably 50-100% by mass, further preferably 60-100% by mass, particularly preferable 70-100% by mass. The absorbent structure is formed in a compressed body, which is 0.05-0.50 g/cm$^2$ in density and 10-1000 g/m$^2$ in basic weight. The fiber used as a base raw material may be hydrophilic fiber such as crushed wood pulp, or cotton linter, cross-linked cellulose fiber, rayon, cotton, wool, acetate, vinylon etc. The absorbent structure of the present invention is preferably made by overlaying them in an air-laid manner.

To manufacture the absorbent article of the present invention, the fiber raw material and the particulate water-absorbing agent are first blended or overlaid to be an absorbent structure (core). The core is then sandwiched between a liquid-permeable base raw material (top sheet) and a liquid-impermeable base raw material (back sheet). If necessary, the absorbent article is further provided with an elastic member, a diffusion layer, an adhesive tape etc. to be completed as an absorbent article, that is used for baby disposal diaper, adult disposal diaper, or a sanitary napkin.

The particulate water-absorbing agent of the present invention has an excellent absorbing ability. The absorbing agent may be used for absorbent articles of various sanitary products such as baby disposal diaper, adult disposal diaper, baby diaper, sanitary napkin, incontinence pad etc. It however should be noted that the present invention is not limited to those. The particulate water-absorbing agent of the present invention contained in the water absorbent article is superior in deodorant property, causes little leakage of liquid, thus ensuring comfort and dryness of the article. On this account, the present invention significantly reduces burden of both the user and the care-giver.

EXAMPLES

The present invention will be described in detail by way of Examples and Comparative Examples. Note, however, that the present invention is not to be limited by the following Examples.

Properties of the particulate water-absorbing agent (or water-absorbent resin) and the water absorbent article were measured in accordance with the following method. Further, all the electrical instruments used in the examples operated on 200 V or 100 V and on 60 Hz. Furthermore, unless otherwise specified, the water-absorbent resin, the particulate water-absorbing agent, and the water absorbent article were used at room temperature (20 to 25° C.) and at a relative humidity of 50%. Further, 0.90% by mass NaCl aqueous solution served as physiological saline solution.

Further, a water-absorbent resin of a commercially available product, a disposal diaper, and a water-absorbent resin of the disposal diaper may be processed in the following manner before use for comparison. When they have already absorbed moisture during the course of distribution, they are dried under reduced pressure (e.g., for 16 hours at 60° C. to 80° C.) until a moisture content of each of the water-absorbent resins is equilibrated (approximately 5% by mass, 2% by mass to 8% by mass). The "moisture content" is defined by the amount of water contained in the water-absorbent resin as measured by the proportion of the lost weight after drying in the mass of the water-absorbent resin before drying when 1 g of the water-absorbent resin is uniformly dispersed into an aluminum cup having a diameter of 52 mm and dried for 3 hours in a windless oven at 180° C. Furthermore, the following method and the reagents and apparatuses exemplified in the Examples may be replaced appropriately by equivalents.

(a) Centrifuge Retention Capacity (CRC) for Physiological Saline Solution (0.90% by Mass NaCl Aqueous Solution)

W (g) (approximately 0.20 g) of each of the particulate water-absorbing agents (or water-absorbent resins) obtained in the following Examples and Comparative Examples was evenly contained in a non woven bag (85 mm×60 mm, EDANA ERT 441.1-99). Then, the non woven bags were sealed. Thereafter, the bags were soaked in physiological saline solution whose temperature had been adjusted to 25±2° C., and were withdrawn 30 minutes later. By using a centrifuge (manufactured by KOKUSAN Corporation: Model No. H-122), the bags were drained for three minutes at 250 G (250×9.81 m/s$^2$), and a mass $W_2$ (g) of each bag was measured. Further, the same procedure was performed without using particulate water-absorbing agent (or water-absorbent resin), and a mass $W_1$ (g) was measured. Then, from the masses $W_1$ and $W_2$, a centrifuge retention capacity (CRC) (g/g) was calculated according to the following equation.

Centrifuge retention capacity (g/g)=((mass $W_2$ (g)−mass $W_1$ (g))/mass $W$ (g)−1

(b) Absorbency Against Pressure at 4.8 kPa for Physiological Saline Solution (AAP/Absorbency Against Pressure)

On a bottom of a plastic supporting cylinder having an internal diameter of 60 mm, a metal gauze of stainless-steel 400 mesh (having a mesh size of 38 μm) was fusion-bonded.

Then, W (g) (approximately 0.90 g) of each of the particulate water-absorbing agents (or water-absorbent resins) obtained in the following Examples and Comparative Examples was uniformly spread on the mesh. Subsequently, a piston (cover plate) was placed on each particulate water-absorbing agent (or water-absorbent resin). External diameters of the piston were slightly smaller than 60 mm which was the internal diameter of the supporting cylinder, so that there is no gap between the piston and the supporting cylinder, and upward and downward movements of the piston would not be hampered. Then the mass $W_3$ (g) was measured, the mass $W_3$ (g) is defined by the masses of the supporting cylinder, the particulate water-absorbing agent (or water-absorbent resin), and the piston. Then, a load was placed on the piston, and the piston and the load were so adjusted as to evenly apply a load of 4.8 kPa onto the particulate water-absorbing agent (or water-absorbent resin). In this way, a set of measuring apparatuses was prepared. Inside a petri dish having a diameter of 150 mm, a glass filter having a diameter of 90 mm and a thickness of 5 mm was placed. Thereafter, physiological saline solution whose temperature had been adjusted to 25±2° C. was added until it reached a level of an upper surface of the glass filter. Then, a piece of filter paper (manufactured by Advantec Toyo Kaisha, Ltd., No. 2) having a diameter of 9 cm was placed thereon, so that an entire surface of the filter paper was wetted. An excess of the physiological saline solution was removed.

The set of measuring apparatuses was placed on the wet filter paper. Then, the particulate water-absorbing agent (or water-absorbent resin) was made to absorb the physiological saline solution for one hour under the load. A level of the physiological saline solution was kept constant by adding the physiological saline solution when the level became lower than that of the upper surface of the glass filter. One hour later, the measuring apparatus set was lifted, and a mass $W_4$ (g) thereof with the load being removed was measured again. The mass $W_4$ (g) is defined by the masses of the supporting cylinder, the swollen particulate water-absorbing agent (or water-absorbent resin), and the piston. From the masses $W_3$ and $W_4$, the absorbency against pressure (g/g) was calculated according to the following equation.

Absorbency against pressure $(g/g)=(W_4 (g)-W_3 (g))/W$ (g)

(c) Mass (weight) average particle diameter (D50), percentage by mass of particles each having a diameter of less than 150 µm, and logarithmic standard deviation (σζ)

Each of the water-absorbent resins or particulate water-absorbing agents obtained in the following Reference Examples, Examples and Comparative Examples was sieved by using JIS standard sieves respectively having mesh sizes of 850 µm, 710 µm, 600 µm, 500 µm, 425 µm, 300 µm, 212 µm, 150 µm, 106 µm, and 45 µm, a weight percentage of particles each having a diameter of less than 150 µm was measured, and a residual percentage R was plotted on a logarithmic probability paper. Then, a particle diameter corresponding to R=50% by mass was read as the mass average particle diameter (D50). Further, assuming that X1 is a particle diameter in case where R=84.1% and X2 is a particle diameter in case where R=15.9%, the logarithmic standard deviation (σζ) is represented by the following equation. A smaller value of σζ means a narrower particle size disribution.

σζ=0.5×ln(X2/X1)

10.00 g of the water-absorbent resin or the particulate water-absorbing agent was spread on the JIS standard sieves (The IIDA TESTING SIEVE: having an internal diameter of 80 mm) respectively having mesh sizes of 850 µm, 710 µm, 600 µm, 500 µm, 425 µm, 300 µm, 212 µm, 150 µm, 106 µm, and 45 µm, and was classified by using a Ro-tap-type sieve shaker (manufactured by IIDA SEISAKUSYO Co., Ltd., Model No. ES-65) for five minutes.

Note that, as described in U.S. Pat. No. 5,051,259, the mass average particle diameter (D50) is a particle diameter of a standard sieve, having a certain mesh size, which corresponds to 50% by mass of the whole particles.

(d) Content (ppm) of an Alcohol Volatile Substance 6.00 g of each of the particulate water-absorbing agents (or water-absorbent resins) obtained in the following Examples and Comparative Examples was uniformly dispersed in a petri dish (described in GENERAL CATALOGUE A-1000 issued by SOGO LABORATORY GLASS WORKS CO., LTD. (in 2003); Code No. 305-07; external diameter× height=120 mm×25 mm). Then, the particulate water-absorbing agents (or water-absorbent resins) were covered by a cut-in-circle piece (having a diameter of 160 mm) of Heatron Paper (manufactured by Nangoku Pulp Kogyo Co., Ltd., Model No. GSP-22), which lets both gas and liquid through (When Heatron Paper is not available, a non woven fabric may be used instead). Thereafter, three portions of the circular piece of Heatron Paper (or non woven fabric) were fixed to an inner wall of the petri dish by respectively using tapes (10 mm×10 mm). A side of a 3-liter scent bag (manufactured by OMI Odor Air Service Co., Ltd.) was opened. The petri dish, in which the particulate water-absorbing agent (or water-absorbent resin) had been dispersed, was enclosed in the bag. The opening of the scent bag was closed by using an adhesive tape so that there was no gap. The scent bag was provided with a glass tube through which air is evacuated from the scent bag. After the evacuation, 1.2 L of odor-free air was injected into the bag. Subsequently, 30 ml of 0.90% by mass NaCl aqueous solution (physiological saline solution) whose temperature had been adjusted to 25±2° C. was poured at once into the petri dish in the scent bag by using a glass funnel provided with a teflon (registered trademark) tube, while preventing outside air from entering into the bag. The particulate water-absorbing agent (or water-absorbent resin) was uniformly swollen. The glass tube of the bag was sealed hermetically by using a silicon rubber stopper. The water-absorbing agent (or water-absorbent resin) was swollen and left in a constant-temperature apparatus at 37° C. The bag was taken out 60 minutes later and then left at room temperature. The silicon rubber stopper was removed ten minutes later. Thereafter, an atmosphere concentration was measured by using a gas sampler (manufactured by GASTEC CORPORATION, Model No. GV-100S) and a gas detecting tube (manufactured by Gas Tech Co., Ltd., Model No. 111LL), while preventing outside air from entering into the bag. This atmosphere concentration was regarded a content (ppm) of an alcohol volatile substance evaporating from the water-absorbing agent. In this measuring method, even when the same operations are performed by using physiological saline solution alone without using the particulate water-absorbing agent, the gas detecting tube may detect the alcohol volatile substance and indicate a color change. In this case, the reported value of content of an alcohol-volatile substance was corrected by subtracting a blank experiment value detected from the indicator range at the time of using only physiological saline solution (detection limit: 2 ppm).

(e) Content (ppm) of a Sulfuric Volatile Substance (Quantity of a Volatile Sulfuric Substance)

An atmosphere concentration was measured by repeating the same operations as the measurement of the alcohol volatile substance, except that a gas detecting tube (manufactured by Gas Tech Co., Ltd., Model No. 4LT) was used. This value of atmosphere concentration was regarded a quantity (ppm) of a sulfuric volatile substance. In this measuring method, even when the same procedure is performed by using physiological saline solution alone without using the particulate water-absorbing agent, the gas detecting tube may indicate a color change. In this case, the reported value of content of a sulfuric volatile substance was corrected by subtracting a blank experiment value detected from the indicator range at the time of using physiological saline solution (detection limit: 0.1 ppm).

(f) Content (ppm) of a Residual Monomer 500 mg of each of the particulate water-absorbing agents (or water-absorbent resins) obtained in the following Examples and Comparative Examples was dispersed in 1 L of ion-exchange water. The mixture was stirred for one hour by using a 40 m cylindrical rotor 40 mm in length and 8 mmφ in gauge. Thereafter, the swollen gel was filtered. A residual monomer of the obtained filtrate was analyzed by liquid chromatography so as to determine a quantity of the residual monomer in the particulate water-absorbing agent (or water-absorbent resins).

(g) Content of Residual Ethylene Glycol 2 g of the particulate water-absorbing agent was added into 2 ml of an aqueous solution of methanol (water:methanol=1:2), and the resulting solution was left for ten minutes. Thereafter, 48 ml of methanol was added into the solution, and the resulting solution was rinsed while being shaken by using an ultrasonic generator. After rinsing, the solution was filtered so as to separate a methanol solution, 30 ml of which was evaporated to dryness by using an evaporator. The resulting dried substance was dissolved again in 3 ml of an aqueous solution of a phosphate carrier, thereby producing a measurement sample of residual ethylene glycol. The obtained measured sample was analyzed by liquid chromatography so as to determine a content of the residual ethylene glycol in the particulate water-absorbing agent.

(h) White Index

A luminance index L and chromaticness indices a and b were calculated by using a Hunter calorimeter.

(i) Absorption Rate Evaluation (Vortex Method)

0.02 parts by mass of brilliant blue-FCF, a food additive "Blue No. 1", was added into 1000 parts by mass of physiological saline solution which had been prepared, and a temperature of the physiological saline solution was adjusted to 30° C. 50 ml of the colored physiological saline solution was transferred into a 100 ml beaker and stirred at 600 rpm by using a cylindrical rotor 40 mm in length and 8 mmφ in gauge. During the stirring, 2.0 g of each of the particulate water-absorbing agents (or water-absorbent resin) was poured into the physiological saline solution in the beaker, and an absorption rate (second) was measured. An end-portion was determined in conformity with a standard described in JIS K 7224 (1996) "Testing Method for Water Absorption rate of Super Absorbent Polymers—Descriptions", a time interval between absorption of the physiological saline solution by the particulate water-absorbing agent (or water-absorbent resin) and covering of a stirrer tip by an test solution was measured as an absorption rate (second).

(j) Moisture Absorption Caking Ratio (% by Mass)

2 g of each of the particulate water-absorbing agents (or water-absorbent resins) obtained in the following Examples and Comparative Examples was uniformly dispersed on a bottom of an aluminum cup, the bottom having a diameter of 52 mm and a height of 22 mm. The aluminum cup was quickly placed and left for 60 minutes in a constant-temperature-and-moisture apparatus (PLATIOOUS LUCIFER PL-2G, manufactured by Tabai Espec Corporation) whose temperature and relative humidity had been adjusted to 25° C. and 90%. Thereafter, the particulate water-absorbing agent (or water-absorbent resin) having been absorbed moisture was transferred onto a JIS standard sieve having an inner diameter of 7.5 cm and a mesh size of 2000 μm. At this time, if the particulate water-absorbing agent (or water-absorbent resin) having been absorbed moisture is firmly bonded to the aluminum cup as it is in a moisture absorption caking condition, it must be removed with greatest possible care before being transferred onto the sieve. The particulate water-absorbing agent (or water-absorbent resin) was classified for eight seconds by using a sieve shaker (IIDA SIEVE SHAKER, TYPE: ES-65, SER. No. 0501). Then, a weight $W_5$ (g) of the particulate water-absorbing agent (or water-absorbent resin) which had remained on the sieve and a weight $W_6$ (g) of the particulate water-absorbing agent (or water-absorbent resin) which had passed through the sieve were measured, respectively.

Moisture absorption caking ratio (% by mass)=Weight $W_5$ (g)/(Weight $W_5$ (g)+Weight $W_6$ (g))×100

A moisture absorption caking ratio (% by mass) was calculated in accordance with the foregoing equation. A lower moisture absorption ratio means excellent fluidity after moisture absorption and easier handling of the particulate water-absorbing agent (or water-absorbent resin) in powder form.

(k) Amount of Extractables, Increased Extractables by Deterioration, and Increased Ratio of Extractables by Deterioration According to the method for evaluating a water-soluble component and a urine-resistant property, which is described in one embodiment of Japanese Patent Application No. 96083/2004, an amount of extractables, increased extractables by deterioration, and increased ratio of extractables by deterioration were calculated.

(l) Evaluation of an Absorbent Structure's Performance

An absorbent structure (core) was produced from each of the particulate water-absorbing agents (or water-absorbent resins) in order to evaluate the absorbent structure's performance, and an absorption capacity of the core under pressure (4.8 kPa) was measured.

First, a method for producing a test absorbent structure will be described below.

One part by mass of the below-mentioned particulate water-absorbing agent (or water-absorbent resin) and one part by mass of wood-crushed pulp were dry-mixed by using a mixer. Then, the obtained mixture was dispersed onto a 400-mesh wire screen having a mesh size of 38 μm and formed into a web having a diameter of 60 mm. The web was subjected to a pressure of 196.14 kPa (2 kgf/cm$^2$) for one minute. As a result, a test absorbent structure having a basic weight of approximately 250 g/cm$^2$ was obtained.

Next, a method for evaluating an absorption capacity of the core under pressure (4.8 kPa) will be described below.

Measurement was carried out according to the method described in (b), so as to evaluate an absorbency against pressure at 4.8 kPa for physiological saline solution (AAP). However, this time, the test absorbent structure was placed instead of the particulate water-absorbing agent on the mesh at the bottom of the plastic supporting cylinder and that the physiological saline solution was absorbed for ten minutes. Then, an absorbed amount of the physiological saline solution was measured as an absorption capacity (g) of the core under pressure (4.8 kPa).

[Example Method for Producing Acrylic Acid]

Commercially-available acrylic acid (2000 ppm of acrylic acid dimer, 500 ppm of acetic acid, 500 ppm of propionic acid, and 200 ppm of p-methoxyphenol) was fed onto a bottom of a high boiling point impurity separating tower having 50 ingate-free porous plates, and was distilled with a reflux ratio of 1, so that malenic acid, acrylic acid dimer (dimer made up of acrylic acid), and other substances were removed. Thereafter, further crystallization was carried out so as to obtain acrylic acid (20 ppm of acrylic acid dimer, 50 ppm of acetic acid, 50 ppm of propionic acid, 1 ppm or less of furfural, and 1 ppm of less of protoanenen). The acrylic acid was further distilled, and 50 ppm of p-methoxyphenol was added into the acrylic acid.

[Method for Producing an Aqueous Solution of Sodium Acrylate]

According to Example 9 of U.S. Pat. No. 5,210,298, 1390 g of the acrylic acid was neutralized at 20° C. to 40° C. by using 48% caustic soda, so that an aqueous solution of sodium acrylate with a concentration of 37% and with a neutralization ratio of 100% was obtained.

Reference Example 1

Acrylic acid was obtained by the foregoing method. An aqueous solution of sodium acrylate was produced from the acrylic acid through the foregoing method. An aqueous solution of sodium acrylate with a neutralization ratio of 75% (with a monomer concentration of 38%) was obtained by mixing the acrylic acid, the aqueous solution of sodium acrylate with a neutralization ratio of 100% and deionized water. A reaction solution was obtained by dissolving 4.3 g of polyethyleneglycoldiacrylate (average added mole number of ethylene oxide: 9) in 5500 g of the aqueous solution of sodium acrylate with a neutralization ratio of 75%, which was obtained by mixing the acrylic acid, the aqueous solution of sodium acrylate with a neutralization ratio of 100%, and deionized water. Then, the reaction solution was fed into a reactor that had been prepared by placing a lid on a 10 L stainless-steel double-arm kneader equipped with two sigma-shaped blades and a jacket. Inside the reactor was replaced with nitrogen gas and dissolved oxygen in the reaction solution was removed while maintaining the temperature of the reaction solution at 30° C. Subsequently, 28.3 g of 10% by mass sodium persulfate aqueous solution and 1.5 g of 1% by mass L-ascorbic acid aqueous solution were added to the reaction solution while the reaction solution was stirred. Approximately one minute later, polymerization was initiated. In 17 minutes after the polymerization was initiated, the polymerization peak temperature reached 86° C. In 40 minutes after the polymerization was initiated, a water-containing gelled polymer was obtained. The obtained water-containing gelled polymer had been crushed into particles having diameters of approximately 1 mm to 4 mm. The crushed water-containing gelled polymer was spread out on a wire mesh with 50 meshes (having a mesh size of 300 µm), and was dried by hot air at 160° C. for 60 minutes. The dry substance was pulverized by using a rolling mill, and then classified by using a wire mesh having a mesh size of 600 µm. As a result, a water-absorbent resin (a) in irregularly pulverized shape was obtained. A particle size distribution of the water-absorbent resin (a) is shown in Table 2.

Reference Example 2

The dry substance obtained in Reference Example 1 was pulverized by using a rolling mill, and then classified and blended by using a wire mesh having a mesh size of 850 µm. Thus, a water-absorbent resin (b) in irregularly pulverized shape was obtained. A particle size distribution of the water-absorbent resin (b) is shown in Table 2.

Reference Example 3

Acrylic acid was obtained by the foregoing method. An aqueous solution of sodium acrylate was produced from the acrylic acid through the foregoing method. An aqueous solution of sodium acrylate with a neutralization ratio of 75% (with a monomer concentration of 38%) was obtained by mixing the acrylic acid, the aqueous solution of sodium acrylate with a neutralization ratio of 100% and deionized water. A reaction solution was obtained by dissolving 7.5 g of polyethyleneglycoldiacrylate (average added mole number of ethylene oxide: 9) in 5500 g of the aqueous solution of sodium acrylate, which is obtained by mixing the acrylic acid, the aqueous solution of sodium acrylate with a neutralization ratio of 100% and deionized water. Then, the dissolved oxygen of the reaction solution was removed in the same manner as in Reference Example 1 and was fed into the reactor of Reference Example 1. Inside the reactor was replaced with nitrogen gas while maintaining the temperature of the reaction solution at 30° C. Subsequently, 28.3 g of 10% by mass sodium persulfate aqueous solution and 1.5 g of 1% by mass L-ascorbic acid aqueous solution were added to the reaction solution, while the reaction solution was stirred.

Approximately one minute later, polymerization was initiated.

In 17 minutes after the polymerization was initiated, the polymerization peak temperature reached 86° C. In 40 minutes after the polymerization was initiated, a water-containing gelled polymer was obtained. The obtained water-containing gelled polymer had been crushed into particles having diameters of approximately 1 mm to 4 mm. The crushed water-containing gelled polymer was spread out on a wire mesh of 50 meshes (having a mesh size of 300 µm), and was dried by hot air at 160° C. for 60 minutes. The dry substance was pulverized by using a rolling mill, and then classified by using a wire mesh having a mesh size of 600 µm.

As a result, a water-absorbent resin (c) in irregularly pulverized shape was obtained. A particle size distribution of the water-absorbent resin (c) is shown in Table 2.

Example 1

0.2 parts by mass of ethylene carbonate, 0.2 parts by mass of glycerin, 3.4 parts by mass of aqueous solution of a surface-cross-linking agent containing 3 parts by mass of water were sprayed to 100 parts by mass of the water-absorbent resin (a) made in [Reference Example 1]. The resulting mixture was heated at a particle temperature of 195° C. for 45 minutes while replacing the internal upper gas with the outside air, by using a paddle-type mixing heating device, thereby obtaining a water-absorbent resin (1) with a cross-linked surface. This water-absorbent resin (1) with a cross-linked surface was passed through a sieve with 710 µm meshes, thereby obtaining a particulate water-absorbing agent (1). For this particulate water-absorbing agent (1), Tables 1 and 2 show: centrifuge retention capacity, absorbency against pressure of 4.8 kPa; absorption rate; particle size distribution, L-value (white index); a-value; b-value; content of alcohol volatile substance; content of sulfuric volatile substance; content of residual monomer; and content of residual ethylene glycol.

Example 2

0.2 parts by mass of ethylene carbonate, 0.3 parts by mass of 1,3-propanediol, 3.5 parts by mass of an aqueous solution of a surface-cross-linking agent containing 3 parts by mass of water were sprayed to 100 parts by mass of the water-absorbent resin (a) made in [Reference Example 1]. The resulting mixture was heated at a particle temperature of 195° C. for 45 minutes while replacing the internal upper gas with the outside air, by using a paddle-type mixing heating device, thereby obtaining a water-absorbent resin (2) with a cross-linked surface. This water-absorbent resin (2) with a cross-linked surface was mixed with 2 parts by mass of an aqueous solution so that the content of pentasodium diethylenetriaminepentaacetate becomes 50 ppm with respect to the whole water-absorbing agent (2) with a cross-linked surface. The resulting mixture was cured for an hour at 60° C., and then was passed through a sieve with 710 μm meshes, thereby obtaining a particulate water-absorbing agent (2). For this particulate water-absorbing agent (2), Tables 1 and 2 show: centrifuge retention capacity; absorbency against pressure of 4.8 kPa; absorption rate; particle size distribution, L-value (white index); a-value; b-value; content of alcohol volatile substance; content of sulfuric volatile substance; content of residual monomer; and content of residual ethylene glycol. The extractables were 8% by mass, and the extractables after deterioration per hour were 10% by mass.

Comparative Example 1

0.05 parts by mass of ethylene glycol deglycidylether, 0.3 parts by mass of 1,4-butanediol, 0.5 parts by mass of propyleneglycol, 3.85 parts by mass of an aqueous solution of a surface-cross-linking agent containing 3 parts by mass of water were sprayed to 100 parts by mass of the water-absorbent resin (a) made in [Reference Example 1]. The resulting mixture was heated at a particle temperature of 195° C. for 45 minutes while replacing the internal upper gas with the outside air, by using a paddle-type mixing heating device, thereby obtaining a comparative water-absorbent resin (1) with a cross-linked surface was passed through a sieve with 710 μm meshes, thereby obtaining a comparative particulate water-absorbing agent (1). For this comparative particulate water-absorbing agent (1), Tables 1 and 2 show: centrifuge retention capacity; absorbency against pressure of 4.8 kPa; absorption rate; particle size distribution, L-value (white index); a-value; b-value; content of alcohol volatile substance; content of sulfuric volatile substance; content of residual monomer; and content of residual ethylene glycol.

Comparative Example 2

0.5 parts by mass of ethylene carbonate, 4.5 parts by mass of a surface-cross-linking agent containing 2 parts by mass of water and 2 parts by mass of ethanol were sprayed to 100 parts by mass of the water-absorbent resin (a) made in [Reference Example 1]. The resulting mixture was heated at a particle temperature of 195° C. for 45 minutes in a closed heating oven without replacing the internal upper gas with the outside air, thereby obtaining a comparative water-absorbent resin (2) with a cross-linked surface. This water-absorbing agent with a cross-linked resin (2) was passed through a sieve with 710 μm meshes, thereby obtaining a comparative particulate water-absorbing agent (2). For this comparative particulate water-absorbing agent (2), Tables 1 and 2 show: centrifuge retention capacity; absorbency against pressure of 4.8 kPa; absorption rate; particle size distribution, L-value (white index); a-value; b-value; content of alcohol volatile substance; content of sulfuric volatile substance; content of residual monomer; and content of residual ethylene glycol.

Comparative Example 3

0.2 parts by mass of ethylene carbonate, 0.2 parts by mass of glycerin, 3.4 parts by mass of aqueous solution of a surface-cross-linking agent containing 3 parts by mass of water were sprayed to 100 parts by mass of the water-absorbent resin (b) made in [Reference Example 2]. The resulting mixture was heated at a particle temperature of 200° C. for 45 minutes while replacing the internal upper gas with the outside air, by using a paddle-type mixing heating device, thereby obtaining a comparative water-absorbent resin (3) with a cross-linked surface. This comparative water-absorbent resin (3) with a cross-linked surface was passed through a sieve with 850-μm meshes, thereby obtaining a comparative particulate water-absorbing agent (3). For this particulate water-absorbing agent (3), Tables 1 and 2 show: centrifuge retention capacity, absorbency against pressure of 4.8 kPa; absorption rate; particle size distribution, L-value (white index); a-value; b-value; content of alcohol volatile substance; content of sulfuric volatile substance; content of residual monomer; and content of residual ethylene glycol.

Example 3

0.2 parts by mass of ethylene carbonate, 0.3 parts by mass of 1,3-propanediol, 3.5 parts by mass of aqueous solution of a surface-cross-linking agent containing 3 parts by mass of water were sprayed to 100 parts by mass of the water-absorbent resin (c) made in [Reference Example 3]. The resulting mixture was heated at a particle temperature of 200° C. for 45 minutes while replacing the internal upper gas with the outside air, by using a paddle-type mixing heating device, thereby obtaining a water-absorbent resin (3) with a cross-linked surface. This water-absorbent resin (3) with a cross-linked surface was mixed with 2 parts by mass of an aqueous solution, and the resulting mixture is cured for an hour at 60° C., and then was passed through a sieve with 710 μm meshes, thereby obtaining a particulate water-absorbing agent (3). For this particulate water-absorbing agent (3), Tables 1 and 2 show: centrifuge retention capacity; absorbency against pressure of 4.8 kPa; absorption rate; particle size distribution, L-value (white index); a-value; b-value; content of alcohol volatile substance; content of sulfuric volatile substance; content of residual monomer; and content of residual ethylene glycol.

Example 4

0.2 parts by mass of ethylene carbonate, 0.2 parts by mass of glycerin, 3.4 parts by mass of aqueous solution of a surface-cross-linking agent containing 3 parts by mass of water were sprayed to 100 parts by mass of the water-absorbent resin (c) made in [Reference Example 3]. The resulting mixture was heated at a particle temperature of 200° C. for 45 minutes while replacing the internal upper gas with the outside air, by using a paddle-type mixing heating device, thereby obtaining a water-absorbent resin (4) with a cross-linked surface. This water-absorbent resin (4) with a cross-linked surface was passed through a sieve with 710 μm meshes, thereby obtaining a particulate water-absorbing agent (4). For this particulate water-absorbing agent (4), Tables 1 and 2 show: centrifuge retention capacity; absorbency against pressure of 4.8 kPa; absorption rate; particle size distribution, L-value (white index); a-value; b-value; content of alcohol volatile substance; content of sulfuric volatile substance; content of residual monomer; and content of residual ethylene glycol.

Comparative Example 4

0.3 parts by mass of 1,4-butanediol, 0.5 parts by mass of propyleneglycol, 3.8 parts by mass of aqueous solution of a surface-cross-linking agent containing 3 parts by mass of water were sprayed to 100 parts by mass of the water-absorbent resin (c) made in [Reference Example 3]. The resulting mixture was heated at a particle temperature of 200° C. for 45 minutes while replacing the internal upper gas with the outside air, by using a paddle-type mixing heating device, thereby obtaining a comparative water-absorbent resin (4) with a cross-linked surface. This comparative water-absorbent resin (4) with a cross-linked surface was passed through a sieve with 710 μm meshes, thereby obtaining a comparative particulate water-absorbing agent (4). For this comparative particulate water-absorbing agent (4), Tables 1 and 2 show: centrifuge retention capacity, absorbency against pressure of 4.8 kPa; absorption rate; particle size distribution, L-value (white index); a-value; b-value; content of alcohol volatile substance; content of sulfuric volatile substance; content of residual monomer; and content of residual ethylene glycol.

Example 5

The particulate water-absorbing agent (2) obtained in Example 2 was mixed (dry-blending) with 0.1 parts by mass of particulate calcium stearate (Kanto Chemical Co. Inc.), thereby obtaining a particulate water-absorbing agent (5). Table 3 shows: centrifuge retention capacity; absorbency against pressure of 4.8 kPa; absorption rate, and moisture-absorption caking ratio of the particulate water-absorbing agent (5). For the other factors, such as particle size distribution, L-value (white index); a-value; b-value; content of alcohol volatile substance; content of sulfuric volatile substance; content of residual monomer; and content of residual ethylene glycol, the particulate water-absorbing agent (5) was same as the particulate water-absorbing agent (2) not mixed with calcium stearate.

Example 6

The particulate water-absorbing agent (3) obtained in Example 3 was mixed (dry-blending) with 0.3 parts by mass of particulate silicon dioxide aerosil 200 (Japan Aerosil. Co.), thereby obtaining a particulate water-absorbing agent (6). Table 3 shows: centrifuge retention capacity; absorbency against pressure of 4.8 kPa; absorption rate, and moisture-absorption caking ratio of the particulate water-absorbing agent (6). For the other factors, such as particle size distribution, L-value (white index); a-value; b-value; content of alcohol volatile substance; content of sulfuric volatile substance; content of residual monomer; and content of residual ethylene glycol, the particulate water-absorbing agent (6) was same as the particulate water-absorbing agent (3) not mixed with silicon dioxide.

For comparison, those factors were also measured for the comparative particulate water-absorbing agents (1) and (4). The results are also shown in Table 3.

Example 7

In order to evaluate the absorbing performance of the particulate water-absorbing agent (1) obtained in Example 1, a test absorbent structure (1) was prepared according to the foregoing evaluation method (1) for performance of absorbent structure. The absorption amount of the core (1) was measured under 4.8 kPa. The result is shown in Table 4.

Further, an odor sensory test was carried out for the evaluated absorbent structure with 10 adult evaluators. The evaluators decided the level of the odor from level 0 (no odor is sensed) to level 5 (odor is sensed) depending on the strength of odor. The average level was determined as an odor point. A lower odor point indicates less significant odor.

These results are also shown in Table 4.

Examples 8 Through 10

The same steps as those in Example 7 were carried out with the particulate water-absorbing agents (3), (5) and (6), instead of the particulate water-absorbing agent (1), thereby obtaining test absorbent structures (2) through (4). The obtained absorbent structures were evaluated in the same manner as that of Example 7. The results are shown in Table 4.

Example 11

0.2 parts by mass of 3-ethyl-3-hydroxymethyloxetane, 0.3 parts by mass of 1,3-propanediol, 3.5 parts by mass of aqueous solution of a surface-cross-linking agent containing 3 parts by mass of water were sprayed to 100 parts by mass of the water-absorbent resin (c) made in [Reference Example 3]. The resulting mixture was heated at a particle temperature of 200° C. for 45 minutes while replacing the internal upper gas with the outside air, by using a paddle-type mixing heating device, thereby obtaining a water-absorbent resin (7) with a cross-linked surface. This water-absorbent resin (7) with a cross-linked surface was passed through a sieve with 710 μm meshes, thereby obtaining a particulate water-absorbing agent (7). For this particulate water-absorbing agent (7), Tables 1 and 2 show: centrifuge retention capacity; absorbency against pressure of 4.8 kPa; absorption rate; particle size distribution, L-value (white index); a-value; b-value; content of alcohol volatile substance; content of sulfuric volatile substance; content of residual monomer; and content of residual ethylene glycol.

Example 12

The same steps as those in Comparative Example 2 were carried out using a paddle-type mixing heating device instead of a closed heating oven, so that the mixture was heated at a particle temperature of 195° C. for 45 minutes while replacing the internal upper gas with the outside air. The heated particles were then exposed to hot airflow of 90° C., whose linear velocity was 1 m/s, for 60 minutes, thereby obtaining a water-absorbent resin (8). For this water-absorbent resin (8) with a cross-linked surface, Tables 1 and 2 show: absorbency against pressure under a centrifuge retention capacity of 4.8 kPa; absorption rate; particle size distribution, L-value (white index); a-value; b-value; content of alcohol volatile substance; content of sulfuric volatile substance; content of residual monomer; and content of residual ethylene glycol.

Example 13

0.1 parts by mass of ethanol amine and an aqueous solution containing 1.9 parts by mass of water were sprayed to the water-absorbent resin (4) obtained in Example 4. The obtained mixture was cured by being exposed to hot airflow of 90° C., whose linear velocity was 1 m/s, for 60 minutes. The obtained particles were then passed through a sieve with 710 μm meshes, thereby obtaining a particulate water-absorbing agent (9). For this particulate water-absorbing agent (9), Tables 1 and 2 show: absorbency against pressure under a centrifuge retention capacity of 4.8 kPa; absorption rate; particle size distribution, L-value (white index); a-value; b-value; content of alcohol volatile substance; content of sulfuric volatile substance; content of residual monomer; and content of residual ethylene glycol.

Comparative Examples 5 Through 8

The same steps as those in Example 7 were carried out with the comparative particulate water-absorbing agents (1) through (4), instead of the particulate water-absorbing agent (1), thereby obtaining test absorbent structures (1) through (4). The obtained absorbent structures were evaluated in the same manner as that of Example 7. The results are shown in Table 4.

TABLE 1

| | PARTICULATE WATER-ABSORBING AGENT | CENTRIFUGE RETENTION CAPACITY (g/g) | ABSORBENCY AGAINST PRESSURE OF 4.8 KPa (g/g) | ABSORPTION-RATE (sec.) | WHITE INDEX L-VALUE/ a-VALUE/ b-VALUE/ |
|---|---|---|---|---|---|
| EXAMPLE 1 | PARTICULATE WATER-ABSORBING AGENT (1) | 34 | 20 | 44 | 94/−0.6/5 |
| EXAMPLE 2 | PARTICULATE WATER-ABSORBING AGENT (2) | 35 | 21 | 45 | 94/−0.6/5 |
| EXAMPLE 3 | PARTICULATE WATER-ABSORBING AGENT (3) | 30 | 25 | 50 | 94/−0.6/5 |
| EXAMPLE 4 | PARTICULATE WATER-ABSORBING AGENT (4) | 29 | 24 | 49 | 94/−0.6/5 |
| EXAMPLE 7 | PARTICULATE WATER-ABSORBING AGENT (7) | 30 | 25 | 50 | 94/−0.6/5 |
| COMPARATIVE EXAMPLE 1 | COMPARATIVE PARTICULATE WATER-ABSORBING AGENT (1) | 35 | 20 | 45 | 94/−0.6/5 |
| COMPARATIVE EXAMPLE 2 | COMPARATIVE PARTICULATE WATER-ABSORBING AGENT (2) | 33 | 19 | 44 | 90/−0.7/5 |
| COMPARATIVE EXAMPLE 3 | COMPARATIVE PARTICULATE WATER-ABSORBING AGENT (3) | 34 | 19 | 49 | 80/−0.2/7 |
| COMPARATIVE EXAMPLE 4 | COMPARATIVE PARTICULATE WATER-ABSORBING AGENT (4) | 29 | 24 | 49 | 94/−0.6/5 |

| | PARTICULATE WATER-ABSORBING AGENT | CONTENT OF ALCOHOL VOLATILE SUB-STANCE (ppm) | CONTENT OF SULFURIC VOLATILE SUB-STANCE (ppm) | RESIDUAL ETHYLENE GLYCOL RESIDUE (ppm) | RESIDUAL MONOMER (ppm) |
|---|---|---|---|---|---|
| EXAMPLE 1 | PARTICULATE WATER-ABSORBING AGENT (1) | 0 | 0 | 0 | 200 |
| EXAMPLE 2 | PARTICULATE WATER-ABSORBING AGENT (2) | 0 | 0 | 0 | 200 |
| EXAMPLE 3 | PARTICULATE WATER-ABSORBING AGENT (3) | 0 | 0 | 0 | 210 |
| EXAMPLE 4 | PARTICULATE WATER-ABSORBING AGENT (4) | 0 | 0 | 0 | 210 |
| EXAMPLE 7 | PARTICULATE WATER-ABSORBING AGENT (7) | 0 | 0 | 0 | 210 |
| COMPARATIVE EXAMPLE 1 | COMPARATIVE PARTICULATE WATER-ABSORBING AGENT (1) | 21 | 0 | 0 | 200 |
| COMPARATIVE EXAMPLE 2 | COMPARATIVE PARTICULATE WATER-ABSORBING AGENT (2) | 12 | 0 | 92 | 200 |
| COMPARATIVE EXAMPLE 3 | COMPARATIVE PARTICULATE WATER-ABSORBING AGENT (3) | 0 | 0 | 48 | 200 |
| COMPARATIVE EXAMPLE 4 | COMPARATIVE PARTICULATE WATER-ABSORBING AGENT (4) | 56 | 0 | 0 | 210 |

TABLE 2

| | PARTICULATE WATER-ABSORBING AGENT | NOT LESS THAN 850 μm (MASS %) | NOT LESS THAN 710 μm LESS THAN 850 μm (MASS %) | NOT LESS THAN 600 μm LESS THAN 710 μm (MASS %) | NOT LESS THAN 500 μm LESS THAN 600 μm (MASS %) | NOT LESS THAN 425 μm LESS THAN 500 μm (MASS %) | NOT LESS THAN 300 μm LESS THAN 425 μm (MASS %) |
|---|---|---|---|---|---|---|---|
| REFERENCE EXAMPLE 1 | WATER-ABSORBENT RESIN (a) | 0.0 | 0.0 | 1.4 | 6.0 | 10.5 | 44.0 |
| REFERENCE EXAMPLE 2 | WATER-ABSORBENT RESIN (b) | 0.0 | 0.9 | 12.5 | 14.8 | 10.8 | 23.9 |
| REFERENCE EXAMPLE 3 | WATER-ABSORBENT RESIN (c) | 0.0 | 0.0 | 1.1 | 6.8 | 11.1 | 49.1 |

TABLE 2-continued

| | | | | | | | |
|---|---|---|---|---|---|---|---|
| EXAMPLE 1 | PARTICULATE WATER-ABSORBING AGENT (1) | 0.0 | 0.4 | 2.1 | 9.1 | 12.9 | 49.4 |
| EXAMPLE 2 | PARTICULATE WATER-ABSORBING AGENT (2) | 0.0 | 0.2 | 1.7 | 8.5 | 12.5 | 49.6 |
| EXAMPLE 3 | PARTICULATE WATER-ABSORBING AGENT (3) | 0.0 | 0.6 | 2.9 | 10.6 | 13.4 | 46.7 |
| EXAMPLE 4 | PARTICULATE WATER-ABSORBING AGENT (4) | 0.0 | 0.5 | 2.2 | 10.6 | 13.4 | 45.9 |
| EXAMPLE 11 | PARTICULATE WATER-ABSORBING AGENT (7) | 0.0 | 0.5 | 2.2 | 10.6 | 13.4 | 45.9 |
| EXAMPLE 12 | PARTICULATE WATER-ABSORBING AGENT (8) | 0.0 | 0.3 | 1.7 | 10.0 | 12.0 | 47.2 |
| EXAMPLE 13 | PARTICULATE WATER-ABSORBING AGENT (9) | 0.0 | 0.5 | 3.4 | 11.1 | 15.4 | 49.8 |
| COMPARATIVE EXAMPLE 1 | COMPARATIVE PARTICULATE WATER-ABSORBING AGENT (1) | 0.0 | 0.2 | 1.8 | 9.1 | 12.9 | 43.5 |
| COMPARATIVE EXAMPLE 2 | COMPARATIVE PARTICULATE WATER-ABSORBING AGENT (2) | 0.0 | 0.3 | 1.7 | 10.0 | 12.0 | 47.2 |
| COMPARATIVE EXAMPLE 3 | COMPARATIVE PARTICULATE WATER-ABSORBING AGENT (3) | 0.1 | 1.1 | 16.5 | 17.6 | 10.8 | 23.4 |
| COMPARATIVE EXAMPLE 4 | COMPARATIVE PARTICULATE WATER-ABSORBING AGENT (4) | 0.0 | 0.2 | 1.6 | 8.3 | 11.5 | 46.9 |

| | PARTICULATE WATER-ABSORBING AGENT | NOT LESS THAN 212 μm LESS THAN 300 μm (MASS %) | NOT LESS THAN 150 μm LESS THAN 212 μm (MASS %) | NOT LESS THAN 45 μm LESS THAN 150 μm (MASS %) | LESS THAN 45 μm (MASS %) | MASS AVERAGE PARTICLE DIAMETER D50 (μm) | LOGARITHMIC STANDARD DEVIATION (σ ζ) |
|---|---|---|---|---|---|---|---|
| REFERENCE EXAMPLE 1 | WATER-ABSORBENT RESIN (a) | 24.1 | 10.8 | 3.1 | 0.1 | 327 | 0.342 |
| REFERENCE EXAMPLE 2 | WATER-ABSORBENT RESIN (b) | 19.1 | 10.1 | 7.6 | 0.3 | 362 | 0.531 |
| REFERENCE EXAMPLE 3 | WATER-ABSORBENT RESIN (c) | 21.4 | 8.4 | 2.1 | 0.0 | 339 | 0.310 |
| EXAMPLE 1 | PARTICULATE WATER-ABSORBING AGENT (1) | 18.8 | 6.0 | 1.3 | 0.0 | 355 | 0.301 |
| EXAMPLE 2 | PARTICULATE WATER-ABSORBING AGENT (2) | 20.3 | 5.8 | 1.4 | 0.0 | 350 | 0.296 |
| EXAMPLE 3 | PARTICULATE WATER-ABSORBING AGENT (3) | 19.0 | 5.6 | 1.2 | 0.0 | 360 | 0.315 |
| EXAMPLE 4 | PARTICULATE WATER-ABSORBING AGENT (4) | 18.0 | 8.2 | 1.2 | 0.0 | 356 | 0.334 |
| EXAMPLE 11 | PARTICULATE WATER-ABSORBING AGENT (7) | 18.0 | 8.2 | 1.2 | 0.0 | 356 | 0.334 |
| EXAMPLE 12 | PARTICULATE WATER-ABSORBING AGENT (8) | 20.8 | 6.9 | 1.1 | 0.0 | 350 | 0.316 |
| EXAMPLE 13 | PARTICULATE WATER-ABSORBING AGENT (9) | 12.6 | 6.3 | 0.9 | 0.0 | 373 | 0.293 |
| COMPARATIVE EXAMPLE 1 | COMPARATIVE PARTICULATE WATER-ABSORBING AGENT (1) | 22.8 | 7.4 | 2.3 | 0.0 | 344 | 0.333 |
| COMPARATIVE EXAMPLE 2 | COMPARATIVE PARTICULATE WATER-ABSORBING AGENT (2) | 20.8 | 6.9 | 1.1 | 0.0 | 350 | 0.316 |

TABLE 2-continued

| | | | | | | | |
|---|---|---|---|---|---|---|---|
| COMPARATIVE EXAMPLE 3 | COMPARATIVE PARTICULATE WATER-ABSORBING AGENT (3) | 14.7 | 9.6 | 6.1 | 0.1 | 402 | 0.524 |
| COMPARATIVE EXAMPLE 4 | COMPARATIVE PARTICULATE WATER-ABSORBING AGENT (4) | 18.8 | 11.1 | 1.6 | 0.0 | 342 | 0.346 |

TABLE 3

| | PARTICULATE WATER-ABSORBING AGENT | CENTRIFUGE RETENTION CAPACITY (g/g) | ABSORBENCY AGAINST PRESSURE OF 4.8 KPA (g/g) | ABSORPTION RATE (sec.) | MOISTURE ABSORPTION CAKING RATIO (% BY MASS) |
|---|---|---|---|---|---|
| EXAMPLE 5 | PARTICULATE WATER-ABSORBING AGENT (5) | 35 | 21 | 46 | 0 |
| EXAMPLE 6 | PARTICULATE WATER-ABSORBING AGENT (6) | 30 | 23 | 40 | 0 |
| COMPARATIVE EXAMPLE 1 | COMPARATIVE PARTICULATE WATER-ABSORBING AGENT (1) | 35 | 20 | 45 | 73 |
| COMPARATIVE EXAMPLE 4 | COMPARATIVE PARTICULATE WATER-ABSORBING AGENT (4) | 29 | 24 | 49 | 70 |

TABLE 4

| | ABSORBENT STRUCTURE | PARTICULATE WATER-ABSORBING AGENT USED | ABSORPTION CAPACITY OF CORE UNDER PRESSURE OF 4.8 kPa (g) | ODOR SENSORY TEST |
|---|---|---|---|---|
| EXAMPLE 7 | TEST ABSORBENT STRUCTURE (1) | PARTICULATE WATER-ABSORBING AGENT (1) | 20 | 1 |
| EXAMPLE 8 | TEST ABSORBENT STRUCTURE (2) | PARTICULATE WATER-ABSORBING AGENT (5) | 21 | 1 |
| EXAMPLE 9 | TEST ABSORBENT STRUCTURE (3) | PARTICULATE WATER-ABSORBING AGENT (3) | 24 | 1 |
| EXAMPLE 10 | TEST ABSORBENT STRUCTURE (4) | PARTICULATE WATER-ABSORBING AGENT (6) | 25 | 1 |
| COMPARATIVE EXAMPLE 5 | COMPARATIVE TEST ABSORBENT STRUCTURE (1) | COMPARATIVE PARTICULATE WATER-ABSORBING AGENT (1) | 20 | 3 |
| COMPARATIVE EXAMPLE 6 | COMPARATIVE TEST ABSORBENT STRUCTURE (2) | COMPARATIVE PARTICULATE WATER-ABSORBING AGENT (2) | 18 | 2 |
| COMPARATIVE EXAMPLE 7 | COMPARATIVE TEST ABSORBENT STRUCTURE (3) | COMPARATIVE PARTICULATE WATER-ABSORBING AGENT (3) | 17 | 1 |
| COMPARATIVE EXAMPLE 8 | COMPARATIVE TEST ABSORBENT STRUCTURE (4) | COMPARATIVE PARTICULATE WATER-ABSORBING AGENT (4) | 24 | 3 |

As shown in Tables 1 and 2, the particulate water-absorbing agent of the present invention contains neither an alcohol volatile substance nor a sulfuric volatile substance, and causes no odor when the agent is swollen and converted into a gel. The particulate water-absorbing agent is also superior in centrifuge retention capacity, absorbency against pressure, and in absorption rate. Further, by addition of inorganic particles, multivalent metallic salts, or deodorant agents, the particulate water-absorbing agent of the present invention becomes superior in anti-caking property (low blocking rate, see Table 3), urine-resistance, and in deodorant property.

An absorbent article (disposal diaper in Table 4) made of the particulate water-absorbing agent of the present invention ensures an excellent absorbing performance, and therefore the liquid absorbed therein does not easily return.

INDUSTRIAL APPLICABILITY

The present invention relates to a particulate water-absorbing agent containing a water-absorbent resin as a main component. More specifically, the present invention relates to a particulate water-absorbing agent superior in absorbing agent ability, and causes no odor when the agent is used for an absorbent article such as disposal diaper.

By using the particulate water-absorbing agent of the present invention for a thin absorbent structure of disposal diaper or the like, superior absorbing agent ability is ensured compared with a conventional absorbent structure, thereby providing an absorbent structure having less odor.

The invention claimed is:

1. A particulate water-absorbing agent containing a particulate polycarboxylic acid water-absorbent resin surface-cross-linked by a surface-cross-linking agent which forms ester bond with a carboxyl group, the particulate water-absorbing agent satisfying following conditions:
    (a) a centrifuge retention capacity (CRC) for a physiological saline solution being not less than 27 g/g;
    (b) an absorbency against pressure (AAP) of 4.8 kPa for the physiological saline solution being not less than 20 g/g;
    (c) a mass average particle diameter (D50) being 200-450 μm;
    (d) an amount of particles smaller than 150 μm in the particulate water-absorbing agent being 0-5% by mass;
    (e) a logarithmic standard deviation (σζ) of particle size distribution being 0.20-0.40; and
    (f) a content of an alcohol volatile substance evaporated from the particulate water-absorbing agent being 0-10 ppm, the content being measured by a gas detecting tube as an atmosphere concentration.

2. A particulate water-absorbing agent containing a particulate polycarboxylic acid water-absorbent resin surface-cross-linked by a surface-cross-linking agent which contains alkylene carbonate and forms ester bond with a carboxyl group,
    the particulate water-absorbing agent satisfying following conditions:
    (a) a centrifuge retention capacity (CRC) for a physiological saline solution being not less than 27 g/g;
    (b) an absorbency against pressure (AAP) of 4.8 kPa for the physiological saline solution being not less than 20 g/g;
    (c) a mass average particle diameter (D50) being 200-450 μm;
    (d) an amount of particles smaller than 150 μm in the particulate water-absorbing agent being 0-5% by mass;
    (e) a logarithmic standard deviation (σζ) of particle size distribution being 0.20-0.40; and
    (g) a content (determined by HPLC) of residual ethylene glycol in the particulate water-absorbing agent being 0-40 ppm.

3. The particulate water-absorbing agent as set forth in claim 1, further containing an alcohol compound (except for ethylene glycol) selected from: aminoalcohol, alkylene carbonate, and multivalent alcohol.

4. The particulate water-absorbing agent as set forth in claim 1, further containing a component selected from: chelating agent, deodorant agent, multivalent metallic salt, and inorganic particles.

5. The particulate water-absorbing agent as set forth in claim 1, wherein: the surface-cross-linking agent is constituted of at least one compound selected from the group consisting of: glycerin, 1,3-propanediol, ethylene carbonate, 3-ethyl-3-hydroxymethyl oxetane and ethanol amine.

6. The particulate water-absorbing agent as set forth in claim 1, wherein:
    the (h) content of a sulfuric volatile substance evaporated from the particulate water-absorbing agent is 0-10 ppm, the content being measured by a gas detecting tube as an atmosphere concentration.

7. The particulate water-absorbing agent as set forth in claim 1, further satisfying a following condition:
    (i) a total amount (determined by HPLC) of acrylic acid, acetic acid and propionic acid being 0-1000 ppm.

8. The particulate water-absorbing agent as set forth in claim 1, further satisfying a following condition:
    (j) luminance indices L being 80 or greater, a being −2 to 2.5, and b being 0-4, where L denotes a luminance index, and a and b are chromaticness indices, all measured as white indices by a Hunter colorimeter.

9. A high-content absorbent structure formed of (a) the particulate water-absorbing agent as set forth in claim 1 and (b) hydrophilic fiber, wherein a content of the particulate water-absorbing agent with respect to a total content of the particulate water-absorbing agent and the hydrophilic fiber is 30-100% by mass.

10. A manufacturing method of the particulate water-absorbing agent as set forth in claim 1, comprising the steps of:
    (i) subjecting an aqueous solution of an unsaturated monomer, which contains a non-neutralized acrylic acid and/or its salt as a main component, to cross-link-polymerizing in a presence of an internal-cross-linking agent, so as to obtain a cross-linked polymer;
    (ii) drying the cross-linked polymer, and adjusting a particle size distribution of the cross-linked polymer, so as to obtain a water-absorbent resin satisfying following conditions:
    (a) a centrifuge retention capacity (CRC) for a physiological saline solution being not less than 30 g/g;
    (b) a mass average particle diameter (D50) being 200-450 μm;
    (c) an amount of particles smaller than 150 μm in the particulate water-absorbent resin being 0-8% by mass;
    (d) a logarithmic standard deviation (σζ) of particle size distribution being 0.20-0.50;
    (iii) heating a vicinity of a surface of the water-absorbent resin after adding a surface-cross-linking agent forming ester bond; and
    (iv) exposing the water-absorbent resin during or after the heating to airflow at or higher than 60° C.

11. The manufacturing method of a particulate water-absorbing agent as set forth in claim 10, wherein the non-neutralized acrylic acid contains at least one kind of compounds selected from the group consisting of: 10-200 ppm of methoxyphenol; 0-10000 ppm of acetic acid and propionic acid combined together; 0-1000 ppm of acrylic acid dimer; 0-10 ppm of furfural, and 0-10 ppm of protoanemonin, all with respect to a mass of the non-neutralized acrylic acid.

12. The manufacturing method of particulate water-absorbing agent as set forth in claim 10, wherein the surface-cross-linking agent contains alkylene carbonate.

13. The manufacturing method of particulate water-absorbing agent as set forth in claim 12, wherein a content of ethylene glycol in the alkylene carbonate is 0.1% by mass or less with respect to a mass of alkylene carbonate.

* * * * *